United States Patent
Hoseit et al.

(10) Patent No.: US 10,058,284 B2
(45) Date of Patent: Aug. 28, 2018

(54) SIMULTANEOUS IMAGING, MONITORING, AND THERAPY

(71) Applicant: VOLCANO CORPORATION, San Diego, CA (US)

(72) Inventors: Paul Hoseit, El Dorado Hills, CA (US); Scott Huennekens, San Diego, CA (US)

(73) Assignee: VOLCANO CORPORATION, San Diego, CA (US)

( * ) Notice: Subject to any disclaimer, the term of this patent is extended or adjusted under 35 U.S.C. 154(b) by 465 days.

(21) Appl. No.: 14/134,184

(22) Filed: Dec. 19, 2013

(65) Prior Publication Data

US 2014/0180034 A1  Jun. 26, 2014

Related U.S. Application Data

(60) Provisional application No. 61/745,119, filed on Dec. 21, 2012.

(51) Int. Cl.
*A61B 8/12* (2006.01)
*A61B 5/00* (2006.01)
(Continued)

(52) U.S. Cl.
CPC .......... *A61B 5/6847* (2013.01); *A61B 5/0066* (2013.01); *A61B 5/0073* (2013.01); *A61B 5/0086* (2013.01); *A61B 5/4839* (2013.01); *A61B 5/6852* (2013.01); *A61B 8/12* (2013.01); *A61B 8/445* (2013.01); *A61B 18/1492* (2013.01); *A61B 8/488* (2013.01); *A61B 2017/22001* (2013.01); *A61B 2018/0022* (2013.01); *A61B 2018/00422* (2013.01); *A61B 2018/00791* (2013.01); *A61B 2018/00863* (2013.01); *A61B 2218/007* (2013.01); *A61N 7/00* (2013.01); *A61N 2007/0043* (2013.01)

(58) Field of Classification Search
CPC .......... A61B 8/00; A61B 8/06; A61B 8/0891; A61B 18/1492; A61B 18/24; A61B 2018/00577
USPC ................................ 600/437, 439, 443, 459
See application file for complete search history.

(56) References Cited

U.S. PATENT DOCUMENTS

| 3,301,258 A | 1/1967 | Werner |
| 3,617,880 A | 11/1971 | Cormack et al. |

(Continued)

FOREIGN PATENT DOCUMENTS

| EP | 1041373 A2 | 10/2000 |
| EP | 01172637 A1 | 1/2002 |

(Continued)

OTHER PUBLICATIONS

International Search Report and Written Opinion dated Nov. 2, 2012, for International Patent Application No. PCT/US12/53168, filed Aug. 30, 2013 (8 pages).

(Continued)

*Primary Examiner* — Allen Porter, Jr.

(57) ABSTRACT

Using the disclosed intravascular devices it is possible to image tissues, deliver therapy, and evaluate the tissue after the therapy is delivered. One embodiment is a catheter configured to provide ultrasound imaging, drug delivery, and Doppler flow analysis. The devices can use ultrasound imaging as well as optical coherence tomography (OCT).

21 Claims, 10 Drawing Sheets

(51) Int. Cl.
*A61B 8/00* (2006.01)
*A61B 18/14* (2006.01)
*A61N 7/00* (2006.01)
*A61B 8/08* (2006.01)
*A61B 17/22* (2006.01)
*A61B 18/00* (2006.01)

(56) References Cited

U.S. PATENT DOCUMENTS

| | | |
|---|---|---|
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |
| 4,344,438 A | 8/1982 | Schultz |
| 4,398,791 A | 8/1983 | Dorsey |
| 4,432,370 A | 2/1984 | Hughes et al. |
| 4,552,554 A | 11/1985 | Gould et al. |
| 4,577,543 A | 3/1986 | Wilson |
| 4,676,980 A | 6/1987 | Segal et al. |
| 4,682,895 A | 7/1987 | Costello |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |

(56) References Cited

U.S. PATENT DOCUMENTS

| | | | |
|---|---|---|---|
| 5,713,848 | A | 2/1998 | Dubrul et al. |
| 5,745,634 | A | 4/1998 | Garrett et al. |
| 5,771,895 | A | 6/1998 | Slager |
| 5,779,731 | A | 7/1998 | Leavitt |
| 5,780,958 | A | 7/1998 | Strugach et al. |
| 5,798,521 | A | 8/1998 | Froggatt |
| 5,800,450 | A | 9/1998 | Lary et al. |
| 5,803,083 | A | 9/1998 | Buck et al. |
| 5,814,061 | A | 9/1998 | Osborne et al. |
| 5,817,025 | A | 10/1998 | Alekseev et al. |
| 5,820,594 | A | 10/1998 | Fontirroche et al. |
| 5,824,520 | A | 10/1998 | Mulligan-Kehoe |
| 5,827,313 | A | 10/1998 | Ream |
| 5,830,222 | A | 11/1998 | Makower |
| 5,848,121 | A | 12/1998 | Gupta et al. |
| 5,851,464 | A | 12/1998 | Davila et al. |
| 5,857,974 | A | 1/1999 | Eberle et al. |
| 5,872,829 | A | 2/1999 | Wischmann et al. |
| 5,873,835 | A | 2/1999 | Hastings et al. |
| 5,882,722 | A | 3/1999 | Kydd |
| 5,912,764 | A | 6/1999 | Togino |
| 5,916,194 | A | 6/1999 | Jacobsen et al. |
| 5,921,931 | A | 7/1999 | O'Donnell et al. |
| 5,925,055 | A | 7/1999 | Adrian et al. |
| 5,949,929 | A | 9/1999 | Hamm |
| 5,951,586 | A | 9/1999 | Berg et al. |
| 5,974,521 | A | 10/1999 | Akerib |
| 5,976,120 | A | 11/1999 | Chow et al. |
| 5,978,391 | A | 11/1999 | Das et al. |
| 5,997,523 | A | 12/1999 | Jang |
| 6,021,240 | A | 2/2000 | Murphy et al. |
| 6,022,319 | A | 2/2000 | Willard et al. |
| 6,031,071 | A | 2/2000 | Mandeville et al. |
| 6,036,889 | A | 3/2000 | Kydd |
| 6,043,883 | A | 3/2000 | Leckel et al. |
| 6,050,949 | A | 4/2000 | White et al. |
| 6,059,738 | A | 5/2000 | Stoltze et al. |
| 6,068,638 | A | 5/2000 | Makower |
| 6,074,362 | A | 6/2000 | Jang et al. |
| 6,078,831 | A | 6/2000 | Belef et al. |
| 6,080,109 | A | 6/2000 | Baker et al. |
| 6,091,496 | A | 7/2000 | Hill |
| 6,094,591 | A | 7/2000 | Foltz et al. |
| 6,095,976 | A | 8/2000 | Nachtomy et al. |
| 6,097,755 | A | 8/2000 | Guenther, Jr. et al. |
| 6,099,471 | A | 8/2000 | Torp et al. |
| 6,099,549 | A | 8/2000 | Bosma et al. |
| 6,102,938 | A | 8/2000 | Evans et al. |
| 6,106,476 | A | 8/2000 | Corl et al. |
| 6,120,445 | A | 9/2000 | Grunwald |
| 6,123,673 | A | 9/2000 | Eberle et al. |
| 6,134,003 | A | 10/2000 | Tearney et al. |
| 6,139,510 | A | 10/2000 | Palermo |
| 6,141,089 | A | 10/2000 | Thoma et al. |
| 6,146,328 | A | 11/2000 | Chiao et al. |
| 6,148,095 | A | 11/2000 | Prause et al. |
| 6,151,433 | A | 11/2000 | Dower et al. |
| 6,152,877 | A | 11/2000 | Masters |
| 6,152,878 | A | 11/2000 | Nachtomy et al. |
| 6,159,225 | A | 12/2000 | Makower |
| 6,165,127 | A | 12/2000 | Crowley |
| 6,176,842 | B1 | 1/2001 | Tachibana et al. |
| 6,179,809 | B1 | 1/2001 | Khairkhahan et al. |
| 6,186,949 | B1 | 2/2001 | Hatfield et al. |
| 6,190,353 | B1 | 2/2001 | Makower et al. |
| 6,200,266 | B1 | 3/2001 | Shokrollahi et al. |
| 6,200,268 | B1 | 3/2001 | Vince et al. |
| 6,203,537 | B1 | 3/2001 | Adrian |
| 6,208,415 | B1 | 3/2001 | De Boer et al. |
| 6,210,332 | B1 | 4/2001 | Chiao et al. |
| 6,210,339 | B1 | 4/2001 | Kiepen et al. |
| 6,212,308 | B1 | 4/2001 | Donald |
| 6,231,518 | B1 | 5/2001 | Grabek et al. |
| 6,245,066 | B1 | 6/2001 | Morgan et al. |
| 6,249,076 | B1 | 6/2001 | Madden et al. |
| 6,254,543 | B1 | 7/2001 | Grunwald et al. |
| 6,256,090 | B1 | 7/2001 | Chen et al. |
| 6,258,052 | B1 | 7/2001 | Milo |
| 6,261,246 | B1 | 7/2001 | Pantages et al. |
| 6,275,628 | B1 | 8/2001 | Jones et al. |
| 6,283,921 | B1 | 9/2001 | Nix et al. |
| 6,283,951 | B1 | 9/2001 | Flaherty et al. |
| 6,295,308 | B1 | 9/2001 | Zah |
| 6,299,622 | B1 | 10/2001 | Snow et al. |
| 6,312,384 | B1 | 11/2001 | Chiao |
| 6,325,797 | B1 | 12/2001 | Stewart et al. |
| 6,328,696 | B1 | 12/2001 | Fraser |
| 6,343,168 | B1 | 1/2002 | Murphy et al. |
| 6,343,178 | B1 | 1/2002 | Burns et al. |
| 6,350,240 | B1 | 2/2002 | Song et al. |
| 6,364,841 | B1 | 4/2002 | White et al. |
| 6,366,722 | B1 | 4/2002 | Murphy et al. |
| 6,367,984 | B1 | 4/2002 | Stephenson et al. |
| 6,373,970 | B1 | 4/2002 | Dong et al. |
| 6,375,615 | B1 | 4/2002 | Flaherty et al. |
| 6,375,618 | B1 | 4/2002 | Chiao et al. |
| 6,375,628 | B1 | 4/2002 | Zadno-Azizi et al. |
| 6,376,830 | B1 | 4/2002 | Froggatt et al. |
| 6,379,352 | B1 | 4/2002 | Reynolds et al. |
| 6,381,350 | B1 | 4/2002 | Klingensmith et al. |
| 6,387,124 | B1 | 5/2002 | Buscemi et al. |
| 6,396,976 | B1 | 5/2002 | Little et al. |
| 6,398,792 | B1 | 6/2002 | O'Connor |
| 6,417,948 | B1 | 7/2002 | Chowdhury et al. |
| 6,419,644 | B1 | 7/2002 | White et al. |
| 6,421,164 | B2 | 7/2002 | Tearney et al. |
| 6,423,012 | B1 | 7/2002 | Kato et al. |
| 6,426,796 | B1 | 7/2002 | Pulliam et al. |
| 6,428,041 | B1 | 8/2002 | Wohllebe et al. |
| 6,428,498 | B2 | 8/2002 | Uflacker |
| 6,429,421 | B1 | 8/2002 | Meller et al. |
| 6,440,077 | B1 | 8/2002 | Jung et al. |
| 6,443,903 | B1 | 9/2002 | White et al. |
| 6,450,964 | B1 | 9/2002 | Webler |
| 6,457,365 | B1 | 10/2002 | Stephens et al. |
| 6,459,844 | B1 | 10/2002 | Pan |
| 6,468,290 | B1 | 10/2002 | Weldon et al. |
| 6,475,149 | B1 | 11/2002 | Sumanaweera |
| 6,480,285 | B1 | 11/2002 | Hill |
| 6,491,631 | B2 | 12/2002 | Chiao et al. |
| 6,491,636 | B2 | 12/2002 | Chenal et al. |
| 6,501,551 | B1 | 12/2002 | Tearney et al. |
| 6,504,286 | B1 | 1/2003 | Porat et al. |
| 6,508,824 | B1 | 1/2003 | Flaherty et al. |
| 6,514,237 | B1 | 2/2003 | Maseda |
| 6,520,269 | B2 | 2/2003 | Geiger et al. |
| 6,520,677 | B2 | 2/2003 | Iizuka |
| 6,535,764 | B2 | 3/2003 | Imran et al. |
| 6,538,778 | B1 | 3/2003 | Leckel et al. |
| 6,544,217 | B1 | 4/2003 | Gulachenski |
| 6,544,230 | B1 | 4/2003 | Flaherty et al. |
| 6,545,760 | B1 | 4/2003 | Froggatt et al. |
| 6,546,272 | B1 | 4/2003 | MacKinnon et al. |
| 6,551,250 | B2 | 4/2003 | Khalil |
| 6,566,648 | B1 | 5/2003 | Froggatt |
| 6,570,894 | B2 | 5/2003 | Anderson |
| 6,572,555 | B2 | 6/2003 | White et al. |
| 6,579,311 | B1 | 6/2003 | Makower |
| 6,584,335 | B1 | 6/2003 | Haar et al. |
| 6,592,612 | B1 | 7/2003 | Samson et al. |
| 6,594,448 | B2 | 7/2003 | Herman et al. |
| 6,602,241 | B2 | 8/2003 | Makower et al. |
| 6,611,322 | B1 | 8/2003 | Nakayama et al. |
| 6,611,720 | B2 | 8/2003 | Hata et al. |
| 6,612,992 | B1 | 9/2003 | Hossack et al. |
| 6,615,062 | B2 | 9/2003 | Ryan et al. |
| 6,615,072 | B1 | 9/2003 | Izatt et al. |
| 6,621,562 | B2 | 9/2003 | Durston |
| 6,631,284 | B2 | 10/2003 | Nutt et al. |
| 6,638,227 | B2 | 10/2003 | Bae |
| 6,645,152 | B1 | 11/2003 | Jung et al. |
| 6,646,745 | B2 | 11/2003 | Verma et al. |
| 6,655,386 | B1 | 12/2003 | Makower et al. |
| 6,659,957 | B1 | 12/2003 | Vardi et al. |

(56) References Cited

U.S. PATENT DOCUMENTS

| | | |
|---|---|---|
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,685,648 B2 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |
| 6,709,444 B1 | 3/2004 | Makower |
| 6,712,836 B1 | 3/2004 | Berg et al. |
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B1 | 4/2006 | Ruffa |
| 7,027,743 B2 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |

(56) References Cited

U.S. PATENT DOCUMENTS

| | | |
|---|---|---|
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 9,283,033 B2 * | 3/2016 | Gelfand ............... A61N 7/022 |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |

(56) References Cited

U.S. PATENT DOCUMENTS

| | | |
|---|---|---|
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childlers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0094930 A1* | 5/2006 | Sparks ............... A61B 17/3207 600/104 |
| 2006/0098927 A1 | 5/2006 | Schmidt et al. |
| 2006/0100522 A1* | 5/2006 | Yuan ........................ A61B 8/12 600/466 |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0139633 A1* | 6/2006 | Puppels ............... A61B 5/0071 356/301 |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016054 A1* | 1/2007 | Cao ........................ A61B 8/06 600/459 |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |

(56) References Cited

U.S. PATENT DOCUMENTS

| | | |
|---|---|---|
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1* | 10/2010 | Katoh ............... A61B 18/1492 606/7 |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg et al. |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |

(56) References Cited

U.S. PATENT DOCUMENTS

| | | |
|---|---|---|
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2438877 A2 | 4/2012 |
| GB | 2280261 A | 1/1995 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2009-233001 A | 10/2009 |
| JP | 2011-56786 A | 3/2011 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/044296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 11/2005 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |
| WO | 2008/107905 A2 | 9/2008 |
| WO | 2009/009799 A1 | 1/2009 |
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2011/06886 A2 | 1/2011 |
| WO | 2011/038048 A1 | 3/2011 |

(56) References Cited

FOREIGN PATENT DOCUMENTS

| | | | |
|---|---|---|---|
| WO | 2011/081688 A1 | 7/2011 | |
| WO | 2012/003369 A2 | 1/2012 | |
| WO | 2012/061935 A1 | 5/2012 | |
| WO | 2012/071388 A2 | 5/2012 | |
| WO | 2012/087818 A1 | 6/2012 | |
| WO | 2012/098194 A1 | 7/2012 | |
| WO | 2012/109676 A1 | 8/2012 | |
| WO | 2012/130289 A1 | 10/2012 | |
| WO | 2012/154767 A2 | 11/2012 | |
| WO | 2012/155040 A1 | 11/2012 | |
| WO | 2013/033414 A1 | 3/2013 | |
| WO | 2013/033415 A2 | 3/2013 | |
| WO | 2013/033418 A1 | 3/2013 | |
| WO | 2013/033489 A1 | 3/2013 | |
| WO | 2013/033490 A1 | 3/2013 | |
| WO | 2013/033592 A1 | 3/2013 | |
| WO | 2013/126390 A1 | 8/2013 | |
| WO | 2014/109879 A1 | 7/2014 | |

OTHER PUBLICATIONS

International Search Report and Written Opinion dated Apr. 14, 2014, for International Patent Application No. PCT/US2013/076148, filed Dec. 18, 2013 (8 pages).
International Search Report and Written Opinion dated Apr. 21, 2014, for International Patent Application No. PCT/US2013/076015, filed Dec. 18, 2013 (7 pages).
International Search Report and Written Opinion dated Apr. 23, 2014, for International Patent Application No. PCT/US2013/075328, filed Dec. 16, 2013 (8 pages).
International Search Report and Written Opinion dated Apr. 29, 2014, for International Patent Application No. PCT/US13/76093, filed Dec. 18, 2013 (6 pages).
International Search Report and Written Opinion dated Apr. 9, 2014, for International Patent Application No. PCT/US13/75089, filed Dec. 13, 2013 (7 pages).
International Search Report and Written Opinion dated Feb. 21, 2014, for International Patent Application No. PCT/US13/76053, filed Dec. 18, 2013 (9 pages).
International Search Report and Written Opinion dated Feb. 21, 2014, for International Patent Application No. PCT/US2013/076965, filed Dec. 20, 2013 (6 pages).
International Search Report and Written Opinion dated Feb. 27, 2014, for International Patent Application No. PCT/US13/75416, filed Dec. 16, 2013 (7 pages).
International Search Report and Written Opinion dated Feb. 28, 2014, for International Patent Application No. PCT/US13/75653, filed Dec. 17, 2013 (7 pages).
International Search Report and Written Opinion dated Feb. 28, 2014, for International Patent Application No. PCT/US13/75990, filed Dec. 18, 2013 (7 pages).
International Search Report and Written Opinion dated Jan. 16, 2009, for International Patent Application No. PCT/US08/78963 filed on Oct. 6, 2008 (7 pages).
International Search Report and Written Opinion dated Jul. 30, 2014, for International Patent Application No. PCT/US14/21659, filed Mar. 7, 2014 (15 pages).
International Search Report and Written Opinion dated Mar. 10, 2014, for International Patent Application No. PCT/US2013/076212, filed Dec. 18, 2013 (8 pages).
International Search Report and Written Opinion dated Mar. 11, 2014, for International Patent Application No. PCT/US13/76173, filed Dec. 16, 2013 (9 pages).
International Search Report and Written Opinion dated Mar. 11, 2014, for International Patent Application No. PCT/US13/76449, filed Dec. 19, 2013 (9 pages).
International Search Report and Written Opinion dated Mar. 18, 2014, for International Patent Application No. PCT/US2013/076502, filed Dec. 19, 2013 (7 pages).
International Search Report and Written Opinion dated Mar. 18, 2014, for International Patent Application No. PCT/US2013/076788, filed Dec. 20, 2013 (7 pages).
International Search Report and Written Opinion dated Mar. 19, 2014, for International Patent Application No. PCT/US13/75349, filed Dec. 16, 2013 (10 pages).
International Search Report and Written Opinion dated Mar. 19, 2014, for International Patent Application No. PCT/US2013/076587, filed Dec. 19, 2013 (10 pages).
International Search Report and Written Opinion dated Mar. 19, 2014, for International Patent Application No. PCT/US2013/076909, filed Dec. 20, 2013 (7 pages).
International Search Report and Written Opinion dated Mar. 7, 2014, for International Patent Application No. PCT/US2013/076304, filed Dec. 18, 2013 (9 pages).
International Search Report and Written Opinion dated Mar. 7, 2014, for International Patent Application No. PCT/US2013/076480, filed Dec. 19, 2013 (8 pages).
International Search Report and Written Opinion dated Mar. 7, 2014, for International Patent Application No. PCT/US2013/076512, filed Dec. 19, 2013 (8 pages).
International Search Report and Written Opinion dated Mar. 7, 2014, for International Patent Application No. PCT/US2013/076531, filed Dec. 19, 2013 (10 pages).
Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al. 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.
Kheir et al., 2012, Oxygen Gas-Filled Microparticles Provide Intravenous Oxygen Delivery, Science Translational Medicine 4(140):140ra88 (10 pages).
Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Kozbor et al., 1984, A human hybrid myeloma for production of human monoclonal antibodies, J. Immunol., 133:3001-3005.

(56) References Cited

OTHER PUBLICATIONS

Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barrett's Esophagus, Endoscopy, 32(12):921-930.
Sihan et al., 2008, A novel approach to quantitative analysis of intraluminal optical coherence tomography imaging, Comput. Cardiol:1089-1092
Siwy et al., 2003, Electro-responsive asymmetric nanopores in polyimide with stable ion-current signal, Applied Physics A: Materials Science & Processing 76:781-785.
Smith et al., 1989, Absolute displacement measurements using modulation of the spectrum of white light in a Michelson interferometer, Applied Optics, 28(16):3339-3342.
Smith, 1997, The Scientist and Engineer's Guide to Digital Signal Processing, California Technical Publishing, San Diego, CA:432-436.
Soller, 2003, Polarization diverse optical frequency domain interferometry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60(9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vasc. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).
Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells, EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18(17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radio-frequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt., 11, 063001-1-063001-19.
Yasuno et al., 2004, Polarization-sensitive complex Fourier domain optical coherence tomography for Jones matrix imaging of biological samples, Applied Physics Letters 85(15):3023-3025.
Zhang et al., 2004, Full range polarization-sensitive Fourier domain optical coherence tomography, Optics Express, 12 (24):6033-6039.
Zitova et al., 2003, Image registration methods: A survey. Image and Vision Computing, 21(11):977-1000.
Abdi et al., 2010, Principal component analysis, Wiley Interdisciplinary Reviews: Computational Statistics 2:433-459.
Adler et al., 2007, Phase-Sensitive Optical Coherence Tomography at up to 370,000 Lines Per Second Using Buffered Fourier Domain Mode-Locked Lasers, Optics Letters, 32(6):626-628.
Agresti, 1996, Models for Matched Pairs, Chapter 8, An Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.

(56) References Cited

OTHER PUBLICATIONS

Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"—Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag.
Barnea et al., 1972, A class of algorithms for fast digital image registration, IEEE Trans. Computers, 21(2):179-186.
Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.
Brown, 1992, A survey of image registration techniques, ACM Computing Surveys 24(4):325-376.
Bruining et al., 2009, Intravascular Ultrasound Registration/Integration with Coronary Angiography, Cardiology Clinics, 27(3):531-540.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring—the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329):1078-1080.

Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61(1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radio-frequency ablation lesion formation using an optical coherence tomography forward-imaging catheter, Journal of Biomedical Optics 15(3):030516-1 (3 pages).
Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome, Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion dated Mar. 11, 2014, for International Patent Application No. PCT/US13/75675, filed Dec. 17, 2013 (7 pages).
International Search Report and Written Opinion dated Mar. 19, 2014, for International Patent Application No. PCT/US13/075353, filed Dec. 16, 2013 (8 pages).
Little et al., 1991, The underlying coronary lesion in myocardial infarction:implications for coronary angiography, Clinical Cardiology, 14(11):868-874.
Loo, 2004, Nanoshell Enabled Photonics-Based Imaging and Therapy of Cancer, Technology in Cancer Research & Treatment 3(1):33-40.
Machine translation of JP 2000-097846.
Machine translation of JP 2000-321034.
Machine translation of JP 2000-329534.
Machine translation of JP 2004-004080.
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.

(56) References Cited

OTHER PUBLICATIONS

Marks et al., 1991, By-passing Immunization Human Antibodies from V-gene Libraries Displayed on Phage, J. Mol. Biol. 222:581-597.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome-strategies to preserve vascular access and extremity, Nephrol Dial Transplant 23:19-24.
Miller et al., 2010, The MILLER banding procedure is an effective method for treating dialysis-associated steal syndrome, Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.
Morrison et al., 1984, Chimeric human antibody molecules: mouse antigen-binding domains with human constant region domains, PNAS 81:6851-6855.
Munson et al., 1980, Ligand: a versatile computerized approach for characterization of ligand-binding systems, Analytical Biochemistry, 107:220-239.
Nezam, 2008, High Speed Polygon-Scanner-Based Wavelength-Swept Laser Sources in the Telescope-Less Configuration with Application in Optical Coherence Tomography, Optics Letters 33(15):1741-1743.
Nissen, 2001, Coronary Angiography and Untravascular Ultrasound, American Journal of Cardiology, 87(suppl):15A-20A.
Nitenberg et al., 1995, Coronary vascular reserve in humans: a critical review of methods of evaluation and of interpretation of the results, Eur Heart J. 16(Suppl 1):7-21.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, published on Nov. 12, 2009, as WO 2009/137704, and accompanying English translation of the Notice of Reason(s) for Refusal and machine translations of JP11-56786 and JP2004-290548 (56 pages).
Nygren, 1982, Conjugation of horseradish peroxidase to Fab fragments with different homobifunctional and heterobifunctional cross-linking reagents. A comparative study, J. Histochem. and Cytochem. 30:407-412.
Oesterle et al., 1986, Angioplasty at coronary bifurcations: single-guide, two-wire technique, Cathet Cardiovasc Diagn., 12:57-63.
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.
Oldenburg et al., 2003, Fast-Fourier-Domain Delay Line for In Vivo Optical Coherence Tomography with a Polygonal Scanner, Applied Optics, 42(22):4606-4611.
Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26(1):80-113.
Pain et al., 1981, Preparation of protein A-peroxidase mono conjugate using a heterobifunctional reagent, and its use in enzyme immunoassays, J Immunol Methods, 40:219-30.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultrastructural changes in genetically-altered murine skeletal muscle using polarization-sensitive optical coherence tomography, Optics Express 14(4):1547-1556.
Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Robbin et al., 2002, Hemodialysis Arteriovenous Fistula Maturity: US Evaluation, Radiology 225:59-64.
Rollins et al., 1998, In vivo video rate optical coherence tomography, Optics Express 3:219-229.
Sarunic et al., 2005, Instantaneous Complex Conjugate Resolved Spectral Domain and Swept-Source OCT Using 3×3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vasc Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.

\* cited by examiner

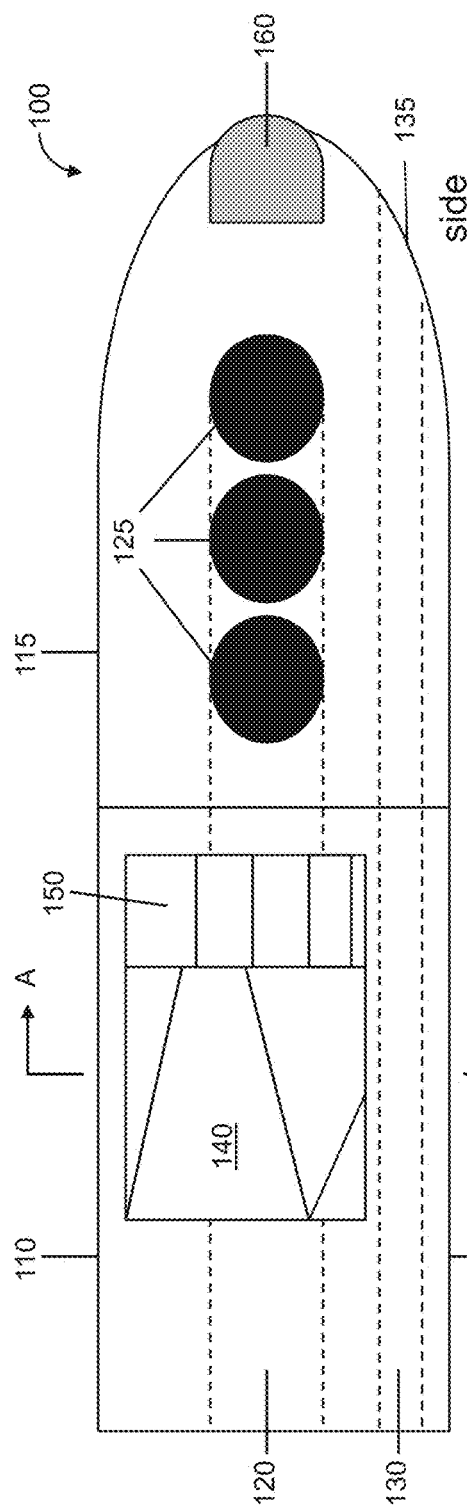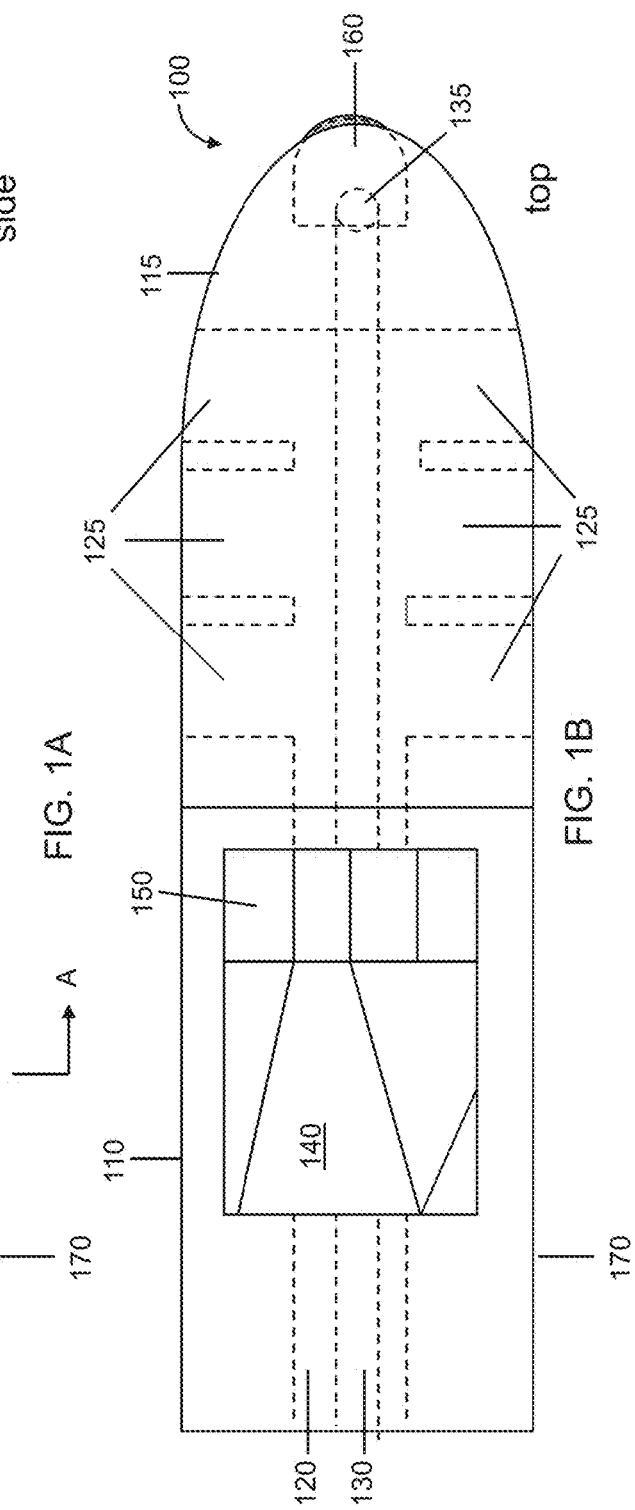
FIG. 1A
FIG. 1B

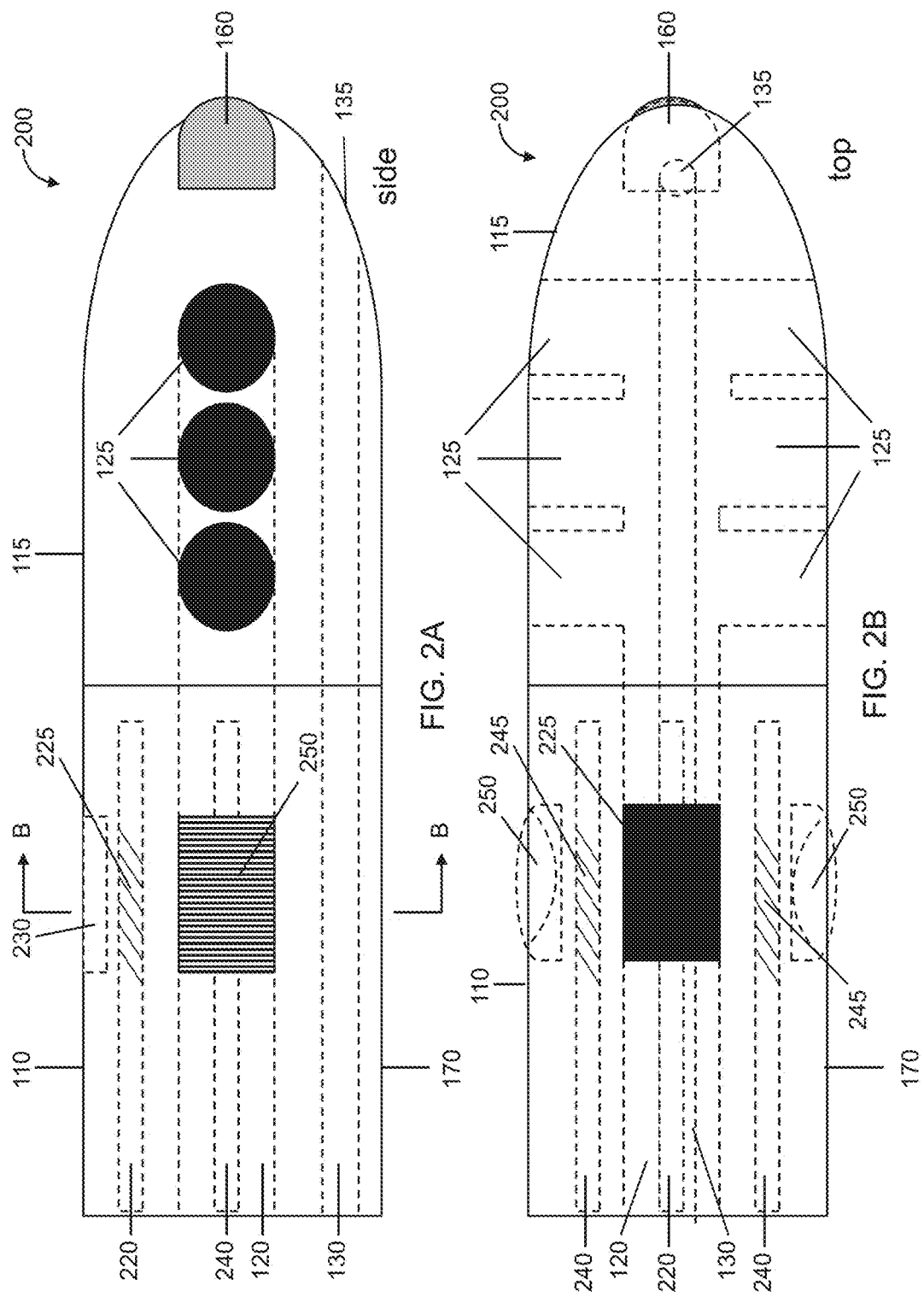

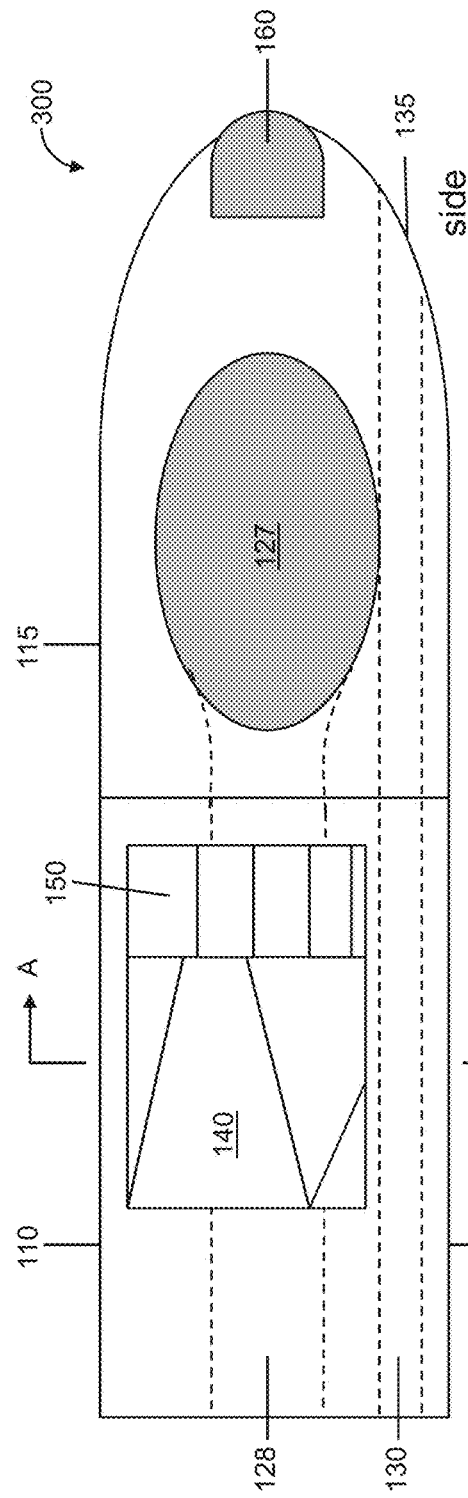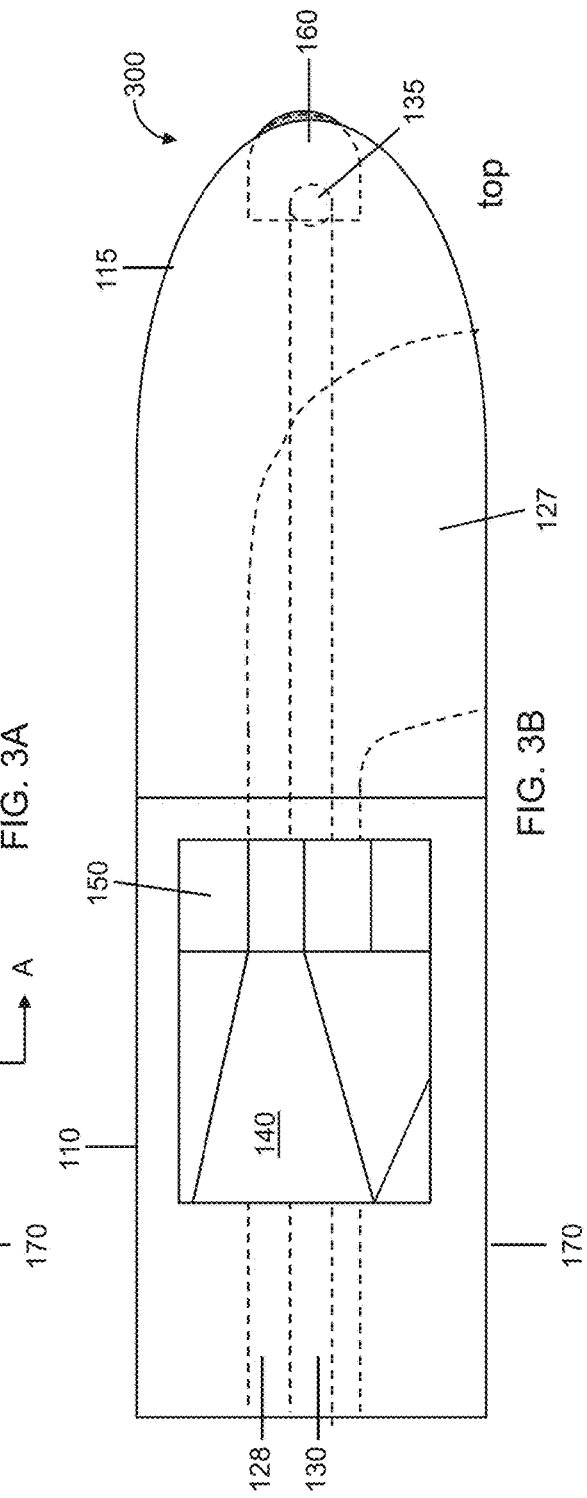
FIG. 3A
FIG. 3B

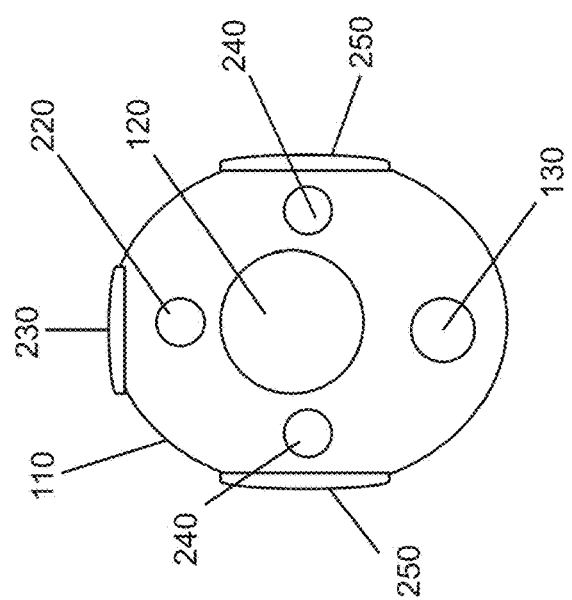
FIG. 4C detail BB
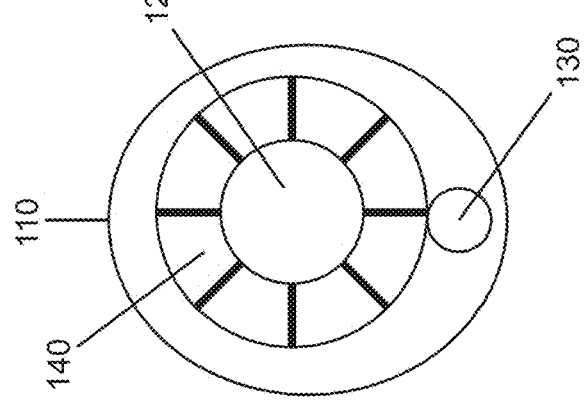
FIG. 4B detail AA
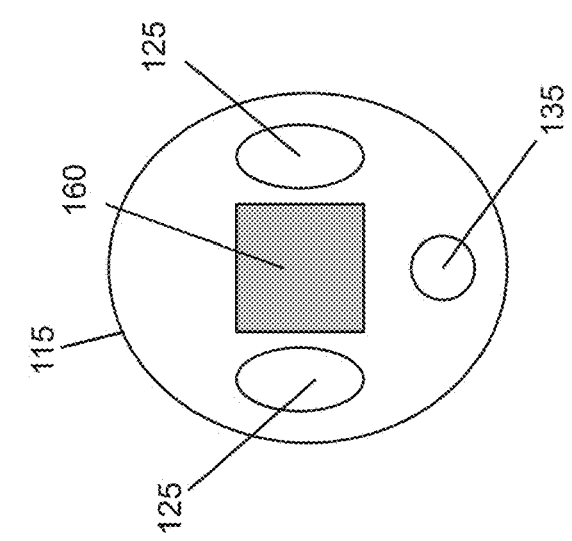
FIG. 4A

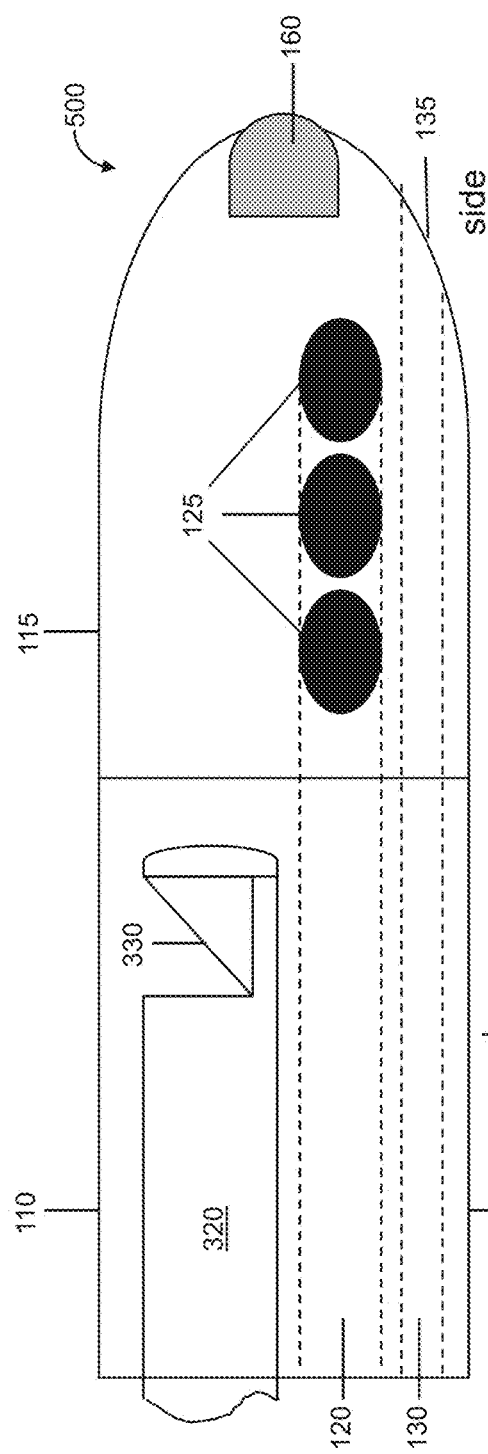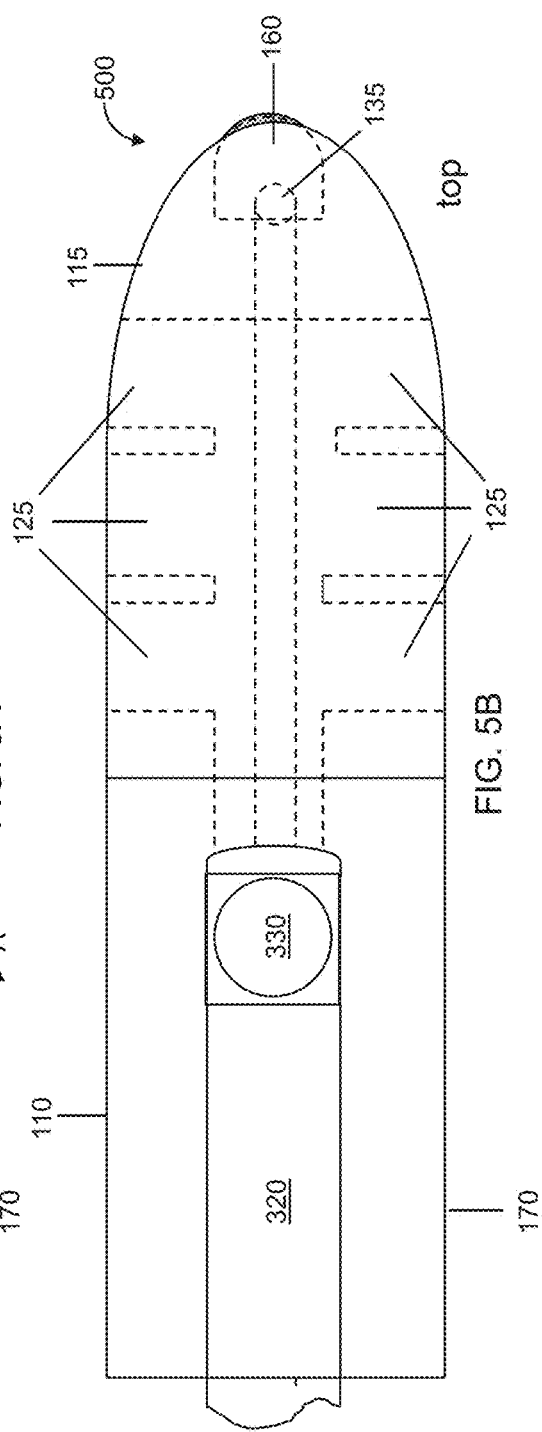
FIG. 5A
FIG. 5B

SIMULTANEOUS IMAGING, MONITORING, AND THERAPY

CROSS-REFERENCE TO RELATED APPLICATIONS

This application claims the benefit of, and priority to, U.S. Provisional Application Ser. No. 61/745,119, filed Dec. 21, 2012, the contents of which are incorporated by reference herein in its entirety.

FIELD OF THE INVENTION

The invention relates to medical devices, such as catheters, that can accomplish multiple tasks at a treatment site, such as imaging, therapeutic delivery, and diagnostic measurement.

BACKGROUND

Endovascular techniques allow a variety of disorders to be evaluated and treated without creating an open surgical field. Such techniques include vascular imaging, aneurism and lesion repair, or even heart valve replacement. Because the techniques are less invasive, they reduce the length of hospital stays associated with treatment, as well as the rate of complications from the treatments. Accordingly, the techniques can reduce costs associated with chronic disease, such as cardiovascular disease.

With current technology, each procedural step typically requires a separate specialized catheter. For example, a patient having a suspected thrombus (blood clot) in an artery will have a guidewire placed in proximity to the occlusion and then an imaging catheter will be delivered to the location to evaluate the site. In particular, the guidewire may be placed within the artery and the imaging catheter may be inserted into the artery by way of the guidewire and positioned at or near the occlusion site. After evaluation, the site may be re-imaged with angiography to verify the location of the defect. The imaging catheter will then be removed, and a new drug delivery catheter will be delivered on the original guidewire. Once delivered, a thrombolytic agent can be administered via the drug delivery catheter. The drug delivery catheter is then removed, and the imaging catheter is replaced to evaluate the success of the thrombolytic agent. Alternatively, a flow-sensing catheter may be used to evaluate the success of the procedure.

Procedures requiring multiple catheter exchanges expose patients to a variety of risks. Because multiple components have to be located within the patient, the patient is exposed to substantial amounts of contrast and x-rays. In addition, each catheter exchange increases the risk of a perforated vessel or other mechanical damage. Exchange procedures can also inadvertently dislodge plaque between the entry point and the treatment site. The dislodged plaque may lead to an embolism or other damage away from the site of treatment.

SUMMARY

The invention facilitates advanced endovascular treatments by providing devices that allow multiple endovascular procedures to be performed with the same device. Because the procedures of the present invention require no, or fewer, catheter exchanges, the procedure can be completed faster than conventional procedures generally requiring multiple exchanges, thereby reducing a patient's exposure to contrast and x-rays, and reducing the cumulative risk of perforation.

The invention includes catheters that can use various combinations of imaging, treatment, and measurement. The imaging may be intravascular ultrasound (IVUS), optical coherence tomography (OCT), or visible imaging. The treatment may be drug delivery, energy therapy (e.g., light or acoustic), aspiration, ablation, angioplasty, debulking, or implant delivery (stent, filter, valve). The measurement may include flow, pressure, temperature, oxygenation, or spectroscopic measurements to determine the presence of specific chemical species. Because the catheters are multifunctional, it will be possible to evaluate a treatment site, administer a treatment, and then re-evaluate the site to determine the success of the treatment. For example, the invention makes it possible to image an arterial lesion with intravascular ultrasound (IVUS), deliver a thrombolytic agent to the lesion, and then measure blood flow in at or near the lesion site in order to gauge the success of the treatment.

The invention is not limited to cardiovascular procedures, however, because devices according to the invention generally provide an ability to image tissue(s), deliver one or more therapies to the tissue(s), and evaluate the success of the therapy. For example, devices of the invention can be used to evaluate a site suspected to be cancerous and deliver therapeutics to the tissues simultaneously with the imaging. Using this technique, a physician can easily treat multiple sites because it is not necessary to change catheters between tumors. Furthermore, there is less risk that a tumor site will be missed because the imaging catheter was removed and the drug delivery catheter was not returned to the correct site. Additionally, because the devices of the invention have such a small diameter, disease sites can be reached through other entry points, such as the urethra.

In one instance, the invention is a device configured to provide acoustic energy to a tissue, receive reflected acoustic energy from the tissue, deliver therapy to the tissue, and measure a property of the tissue, or an environment associated with the tissue. In some embodiments, the device is configured to deliver, for example, a solution comprising a therapeutic agent to a tissue. In some embodiments, the device is configured to image the tissue with intravascular ultrasound (IVUS). Other modes of therapy are additionally available.

In another instance, the invention is a device configured to image a tissue with optical coherence tomography, deliver a therapy, and measure a property of the tissue, or an environment in proximity to the tissue. The device is configured to deliver, for example, a solution comprising a therapeutic agent to a tissue. Other modes of therapy are additionally available.

In another instance, the invention is a system for delivering therapeutic agents to a subject, including a guidewire having an ultrasound transducer, configured to image, monitor, or deliver acoustic therapy to a tissue. The system also includes a catheter having a first lumen in fluid communication with a proximal end and a distal end of the catheter, a second lumen for receiving the guidewire located in proximity to the distal end of the catheter, an ultrasound transducer in communication with a connector located in proximity to the proximal end of the catheter, and an ultrasound receiver in communication with the connector. In some embodiments, the guidewire includes an optical fiber.

In another instance, the invention is a device for delivering therapy to a subject. The device includes a first lumen in fluid communication with a proximal end and a distal end of the device, a second lumen for receiving a guidewire located in proximity to the distal end of the device, an ultrasound transducer in communication with a connector located in proximity to the proximal end of the device, and an ultrasound receiver in communication with the connector. The ultrasound transducer and receiver may each include a piezoelectric element in electrical communication with the connector. The ultrasound transducer may further include a photoacoustic member in optical communication with the connector. The ultrasound receiver may include a photoreflective member in optical communication with the connector. The ultrasound transducer may be configured to produce acoustic energy with a frequency between 15 and 30 MHz and/or between 5 and 15 MHz and/or between 100 kHz and 5 MHz. Further, the ultrasound transducer may be located at a distal tip of the device. The ultrasound transducer may be a pulsed ultrasound transducer.

The device may further include an optical fiber in optical communication with the proximal end and the distal end of the device. The optical fiber may include a blazed Bragg grating. The device may further include a lens located in proximity to the distal end of the device and in optical communication with the optical fiber.

In some embodiments, the first lumen of the device can be used to deliver a therapeutic agent. For example, the first lumen can be used to aspirate a tissue, to inflate a balloon at the distal end of the device, or combinations thereof. The device may further include a port in fluid communication with the proximal end of the first lumen. Further, in some embodiments, the second lumen may be less than 100 mm in length. In some embodiments, the device can be delivered through an introducer having an opening of 12 French or less (4 mm or smaller). Further, the device may include a radiopaque label. In some embodiments, the device may be a catheter.

In another instance, the invention is a system for delivering therapy to a subject. The system includes a guidewire including a guidewire ultrasound transducer in communication with a guidewire connector located at the proximal end of the guidewire. The system further includes a catheter including a first lumen in fluid communication with a proximal end and a distal end of the catheter, a second lumen for receiving the guidewire located in proximity to the distal end of the catheter, a plurality of catheter ultrasound transducers in communication with a connector located in proximity to the proximal end of the catheter, and a plurality of catheter ultrasound receivers in communication with the connector.

In some embodiments, the guidewire additionally includes a guidewire ultrasound receiver in communication with the guidewire connector. In some embodiments, at least one of the guidewire ultrasound transducers and receivers may include a piezoelectric element in electrical communication with the guidewire connector. In some embodiments, at least one of the guidewire ultrasound transducers and receivers may each include a photoacoustic member in optical communication with the guidewire connector. In some embodiments, at least one of the guidewire ultrasound transducers and receivers may each include a photoreflective member in optical communication with the guidewire connector. In some embodiments, at least one of the catheter ultrasound transducers and receivers may include piezoelectric elements in electrical communication with the catheter connector. In some embodiments, the catheter ultrasound transducers may include photoacoustic members in optical communication with the catheter connector. In some embodiments, the catheter ultrasound receivers may include photoreflective members in optical communication with the catheter connector. Further, in some embodiments, the guidewire includes at least one of an optical fiber and a lens.

In another instance, the invention is a system for delivering therapy to a subject. The system includes a guidewire including a guidewire ultrasound transducer in communication with a guidewire connector located at the proximal end of the guidewire. The system further includes a catheter including a first lumen in fluid communication with a proximal end and a distal end of the catheter, a second lumen for receiving the guidewire located in proximity to the distal end of the catheter, and a rotational imaging element.

The invention also provides methods for treating tissues, including imaging a tissue with acoustic energy from a device, administering therapy to the tissue with the device, and measuring a property of an environment associated with the tissue with the device. The imaging includes at least one of IVUS and OCT methods. The administering of therapy to the tissue may include delivering a solution including a therapeutic agent and further administering electromagnetic radiation to the therapeutic agent. The administering of therapy may also, or alternatively, include placing a medical device selected from a strut, stent, valve, or filter.

The property may include blood flow in a vessel, blood pressure in a vessel, blood oxygenation in a vessel, temperature, presence of a chemical species, or a combination thereof. The measuring may include making a spectroscopic measurement selected from infrared absorption, visible absorption, Raman, fluorescence, or combinations thereof. The therapy may also, or alternatively, include aspirating a tissue, angioplasty, and/or ablation.

The invention also provides methods for treating tissues, including imaging a tissue with acoustic energy from a device, administering therapy to the tissue with the device, and administering acoustic therapy to the tissue with the device. The method also includes measuring a property of the tissue or an environment associated with the tissue with the device. The imaging includes at least one of IVUS and OCT methods. The administering of therapy to the tissue may include delivering a solution including a therapeutic agent and further administering electromagnetic radiation to the therapeutic agent. The administering of therapy may also, or alternatively, include placing a medical device selected from a strut, stent, valve, or filter.

The property may include blood flow in a vessel, blood pressure in a vessel, blood oxygenation in a vessel, temperature, presence of a chemical species, or a combination thereof. The measuring may include making a spectroscopic measurement selected from infrared absorption, visible absorption, Raman, fluorescence, or combinations thereof. The therapy may also, or alternatively, include aspirating a tissue, angioplasty, and/or ablation.

These and other aspects, advantages, and features of the invention will be better understood with reference to the following drawings and description.

BRIEF DESCRIPTION OF THE DRAWINGS

FIG. 1A depicts a side view of the distal end of a catheter of the invention;

FIG. 1B depicts a top view of the distal end of a catheter of the invention;

FIG. 2A depicts a side view of the distal end of a catheter of the invention;

FIG. 2B depicts a top view of the distal end of a catheter of the invention;

FIG. 3A depicts a side view of the distal end of a catheter of the invention;

FIG. 3B depicts a top view of the distal end of a catheter of the invention;

FIG. 4A depicts a distal end view of a catheter of the invention;

FIG. 4B depicts a cross-sectional view of the catheter of FIGS. 1A and 1B;

FIG. 4C depicts a cross-sectional view of the catheter of FIGS. 2A and 2B;

FIG. 5A depicts a side view of the distal end of a catheter of the invention;

FIG. 5B depicts a top view of the distal end of a catheter of the invention;

DETAILED DESCRIPTION

Figure 6:
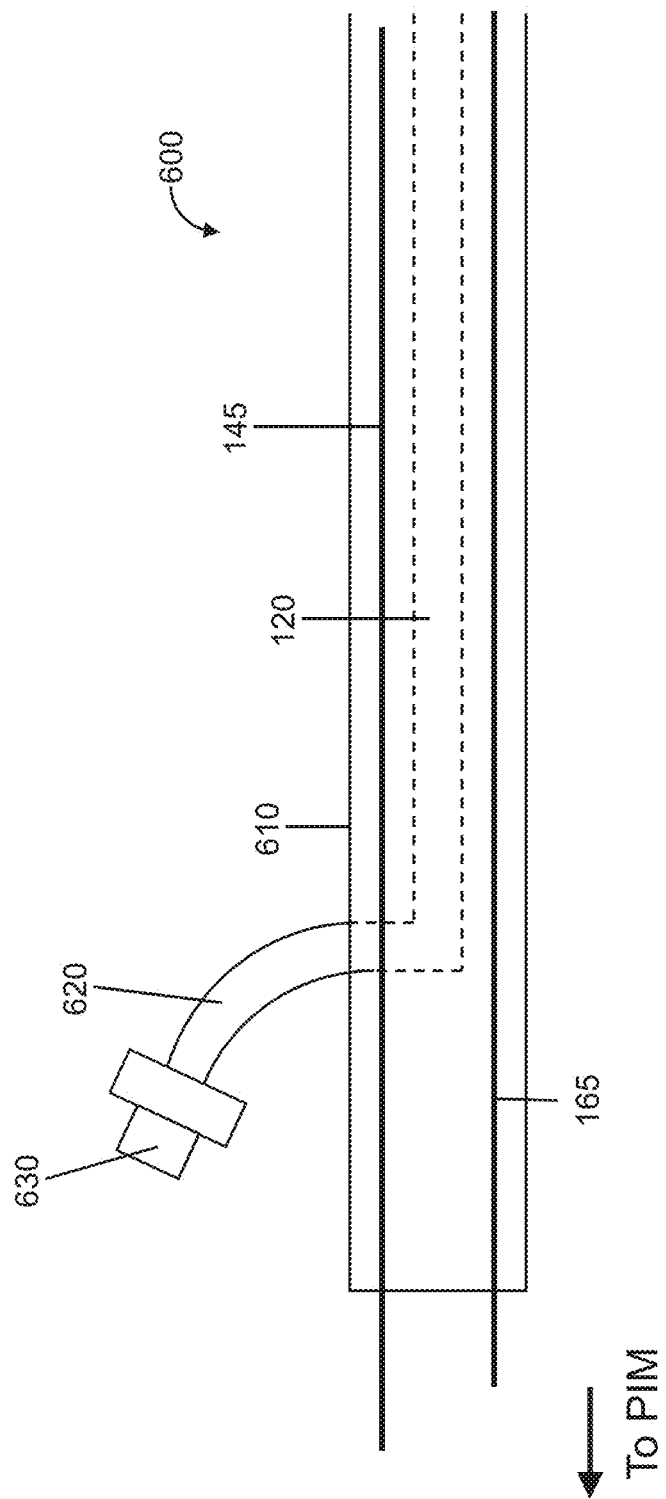
FIG. 6 depicts the proximal end of a catheter of the invention.

The invention provides advanced intraluminal devices configured to image tissues, deliver therapy to the tissues, and monitor the results of the therapy on an environment in proximity to the tissue. The devices allow a variety of treatments to be administered with the devices, including, but not limited to drug delivery, energy therapy (e.g., light or acoustic), aspiration, ablation, angioplasty, debulking, or implant delivery (stent, filter, valve). For example, the invention includes drug delivery catheters that are configured to provide IVUS imaging and Doppler flow monitoring. The devices of the invention may use "conventional" IVUS components, such as piezoelectric transducers, or the devices may use optical IVUS components, described in detail below. The devices may use optical coherence tomography (OCT). The devices lend themselves to methods for the treatment of tissues in need thereof as well as systems including the devices of the invention.

Using the devices of the invention, a variety of target tissues can be imaged, diagnosed, treated, and evaluated with the devices, methods, and systems of the invention. In particular the invention is useful for treating tissues that are accessible via the various lumens of the body, including, but not limited to, blood vessels, vasculature of the lymphatic and nervous systems, structures of the gastrointestinal tract (lumens of the small intestine, large intestine, stomach, esophagus, colon, pancreatic duct, bile duct, hepatic duct), lumens of the reproductive tract (vas deferens, uterus and fallopian tubes), structures of the urinary tract (urinary collecting ducts, renal tubules, ureter, and bladder), and structures of the head and neck and pulmonary system (sinuses, parotid, trachea, bronchi, and lungs). Accordingly, the devices, methods, and systems of the invention may be beneficial in the treatment of a number of disorders, including, but not limited to, atherosclerosis, ischemia, coronary blockages, thrombi, occlusions, stenosis, and aneurysms. The devices, methods, and systems can also be used to treat cancer, inflammatory disease (e.g., autoimmune disease, arthritis), pain, and genetic disorders.

The devices, methods, and systems of the invention can be used to administer a variety of therapeutics, such as thrombolytic agents, anti-cancer agents, anti-inflammatory agents, analgesic agents, or combinations thereof. For example, the therapeutic agent may comprise streptokinases, anistreplases, urokinases, tissue plasminogen activators (t-PA), alteplases, tenecteplases, or reteplases. The devices, methods, and systems of the invention may be used to administer more than one therapeutic or more than one class of therapeutics. For example, a solution delivered to a tissue in need of treatment may comprise a thrombolytic drug and an anti-coagulant, such as heparin.

The devices, methods, and systems of the invention can be used to administer therapy with a catheter. The devices can be used for angioplasty, such as balloon angioplasty. The devices can be used for ablation, such as balloon ablation, or probe ablation. The devices can be used to aspirate or remove tissues. The devices can be used for medical device placement, such as stents, struts, valves, filters, pacemakers, or radiomarkers. The devices, methods, and systems of the invention may be used to administer more than one therapy of combinations of therapies and therapeutics, e.g., drugs. For example, a solution delivered to a tissue in need of treatment may comprise a thrombolytic drug and aspiration.

Devices of the invention are typically catheters. A variety of intravascular catheters are known. In practice, intravascular catheters are delivered to a tissue of interest via an introducer sheath placed in the radial, brachial or femoral artery. The introducer is inserted into the artery with a large needle, and after the needle is removed, the introducer provides access for guidewires, catheters, and other endovascular tools. An experienced cardiologist can perform a variety of procedures through the introducer by inserting tools such as balloon catheters, stents, or cauterization instruments. When the procedure is complete the introducer is removed, and the wound can be secured with suture tape. Catheter lengths vary up to 400 cm, depending on the anatomy and work flow. The ends of the catheter are denoted as distal (far from the user, i.e., inside the body) and proximal (near the user, i.e., outside the body).

An important function of the devices is an ability to image a tissue prior to treatment. In particular, the invention provides devices, systems and methods for imaging tissue using intravascular ultrasound (IVUS). IVUS uses a catheter with an ultrasound probe attached at the distal end. Systems for IVUS are also discussed in U.S. Pat. No. 5,771,895, U.S. Pat. Pub. 2009/0284332, U.S. Pat. Pub. 2009/0195514 A1, U.S. Pat. Pub. 2007/0232933, and U.S. Pat. Pub. 2005/0249391, the entire contents of each of which are incorporated herein by reference.

In some embodiments, the devices are configured to image tissues with optical coherence tomography (OCT), which uses interferometric measurements to determine radial distances and tissue compositions. Systems for OCT imaging are discussed in U.S. Pat. No. 7,813,609 and US Patent Publication No. 20090043191, both of which are incorporated herein by reference in their entireties.

The disclosed devices are commonly used in conjunction with guidewires. Guidewires are known medical devices used in the vasculature or other passageway and act as a guide for other devices, e.g., a catheter. Typically, the guidewire is inserted into an artery or vein and guided through the vasculature under fluoroscopy (real time x-ray imaging) to the location of interest. (As discussed previously, some procedures require one or more catheters to be delivered over the guide wire to diagnose, image, or treat the condition.) Guidewires typically have diameters of 0.010" to 0.035", with 0.014" being the most common. Guidewires (and other intravascular objects) are also sized in units of French, each French being ⅓ of a mm or 0.013". Guidewire lengths vary up to 400 cm, depending on the anatomy and work flow. Often a guidewire has a flexible distal tip portion about 3 cm long and a slightly less flexible portion about 30 to 50 cm long leading up to the tip with the remainder of the guidewire being stiffer to assist in maneuvering the guidewire through tortuous vasculature, etc. The tip of a guidewire typically has a stop or a hook to prevent a guided device, e.g., a catheter from passing beyond the distal tip. In some embodiments, the tip can be deformed by a user to produce a desired shape.

Advanced guidewire designs include sensors that measure flow and pressure, among other things. For example, the FLOWIRE Doppler Guide Wire, available from Volcano Corp. (San Diego, Calif.), has a tip-mounted ultrasound transducer and can be used in all blood vessels, including both coronary and peripheral vessels, to measure blood flow velocities during diagnostic angiography and/or interventional procedures. Advanced guidewires, such as FLOWIRE, can be used with the described inventions. In some instances, an advanced guidewire can be used to supplement the capabilities of the devices of the invention. In some instances, an advanced guidewire can be used to replace a capability (e.g., flow sensing) of a disclosed device. In some instances, and advanced guidewire is incorporated into a system of the invention, e.g., additionally including a catheter described below.

The distal end 110 of a device of the invention (i.e., a catheter) is shown in FIGS. 1A and 1B. FIG. 1A shows a side view of an imaging/delivery/evaluation catheter 100 that uses piezoelectric elements as ultrasound transducers 140 and ultrasound receivers 150 to produce and receive ultrasound energy for imaging. Catheter 100 includes a proximal end (not shown), a mid-body (not shown), and a distal end 110 including a distal tip 115. The distal end 110 includes drug delivery lumen 120 connected to drug delivery ports 125, and guidewire lumen 130 terminating in guidewire exit 135. The distal tip 115 comprises Doppler sensor 160. The entire distal end 110 is coated with a lubricious coating 170, and a suitable ultrasound transparent material is used to cover the ultrasound transducers 140 and ultrasound receivers 150. (The dashed lines indicate that the actual structures are hidden from view in a side or top view of the exterior.)

The ultrasound transducers 140 are constructed from piezoelectric components that produce sound energy at 20-50 MHz. The ultrasound transducers 140 are known in the field of intravascular ultrasound imaging, and are commercially available from suppliers such as Blatek, Inc. (State College, Pa.). As shown in FIGS. 1A and 1B, the ultrasound transducers 140 are configured in a phased array, that is, each ultrasound receiver 150 is a separate piezoelectric element that produces ultrasound energy. Similarly, each ultrasound receiver 150 is an independent element configured to receive ultrasound energy reflected from the tissues to be imaged. Alternative embodiments of the ultrasound transducers 140 and the ultrasound receivers 150 may use the same piezoelectric components to produce and receive the ultrasonic energy, for example, by using pulsed ultrasound. Another alternative embodiment may incorporate ultrasound absorbing materials and/or ultrasound lenses to increase signal to noise. Both the ultrasound transducers 140 and the ultrasound receivers 150 have electrical connectors (not shown) that extend from the transducers 140 and receivers 150 to the proximal end of the device to provide power, and to provide and receive ultrasound signals.

As can be seen more clearly in FIG. 1B, the transducers 140 and receivers 150 are coaxially located with the drug delivery lumen 120 to maximize the inside diameter of the drug delivery lumen 120 with respect to the diameter of the distal end 110 of the device. This detail can also be seen in FIG. 4B, which depicts a cross section from A to A in FIG. 1A. Other embodiments of the invention need not adopt this design. For example drug delivery lumen may run to one side of the ultrasound transducers 140 and receivers 150. Alternatively, drug delivery lumen 120 may comprise multiple lumens that are arranged about the ultrasound transducers 140 and receivers 150 to provide adequate throughput for the delivery of therapeutic agents, typically formulated as a liquid. Additionally, while the views of FIGS. 1A and 1B depict six drug delivery ports 125, this number is arbitrary. The drug delivery lumen 120 merely needs one or more exit ports to allow the therapeutic to be delivered external to the distal end 110.

The Doppler sensor 160, located in the distal tip 115 of the device allows a physician to measure and observe a property of an environment associated with the tissue being imaged and treated. For example, in one embodiment, the tissue being imaged and treated may be an arterial lesion. Accordingly, the Doppler sensor 160 may be configured to measure a property (e.g., blood flow) of an environment associated with the lesion. As generally understood, an environment associated with the lesion may refer any environment that is connected, either directly or indirectly, to the lesion or sharing a common pathway (e.g., artery) with the lesion. For example, the environment may include one or more portions of the lumen of the artery in which the lesion has formed. The one or more portions may include a portion of the lumen adjacent to the lesion or a portion that is located a distance away from the lesion, either downstream or upstream, along a length of the artery. Accordingly, the Doppler sensor 160 can be inserted within the lumen of the artery and positioned at a location of the lumen associated with the lesion, so as to acquire measurements of blood flow in order to gauge the success of treatment to the lesion. For example, the Doppler sensor 160 may be positioned within a portion of the lumen directly adjacent to the lesion and may acquire blow flow data of the artery. In other examples, the Doppler sensor 160 can be positioned in other portions of the lumen (e.g., downstream and a distance away from the lesion, upstream and a distance away from the lesion, locations therebetween, etc.).

The Doppler sensor is electrically connected (not shown) to the proximal end of the device, which provides power for the sensor and a return path for recovering measurements. Typically, the sensor produces ultrasound in the range of 5 to 15 MHz, e.g., about 12 MHz. In other embodiments, the Doppler sensor may be replaced with an acoustic therapy transducer (not shown) to deliver acoustic waves to a tissue being treated. Acoustic therapy transducers typically operate in the range of 100 kHz and 5 MHz. Because the Doppler sensor and the acoustic therapy transducers are rather small, it is also possible for a device to include both a Doppler sensor and an acoustic therapy transducer.

Other sensors can also be accommodated in distal end 110 and are configured to measure one or more properties of an environment associated with the tissue being imaged and treated, as described herein. For example, the distal end 110 may include a thermocouple, a thermistor, or a temperature diode to measure the temperature of the surroundings associated with the tissue. The distal end 110 may include a pressure sensor, such as a piezoelectric pressure sensor, or a semiconductor pressure sensor. The distal end 110 may also include one or more elements to perform spectroscopic measurements, e.g., infrared absorption spectroscopy, visible wavelength absorption spectroscopy, fluorescence spectroscopy, or Raman spectroscopy. In some embodiments, the spectroscopic measurement will rely on collecting backscattered or fluorescent light. In some embodiments, the spectroscopic measurements can be made with optical elements that are also used to make OCT measurements. In some embodiments, the distal end 110 of the catheter will include an optical pathway which is in fluid communication with the surroundings of the catheter, thereby allowing direct absorption measurements, for example, visible absorbance spectroscopy.

Using spectroscopic methods, it is possible to probe a tissue, or the environment around the tissue, for the presence of specific chemical species indicative of the health of the tissue (or the surroundings) or indicative of the efficacy of an administered treatment. The chemical species may include, for example, calcium ions or sodium ions. The methods may also be used to monitor oxygen content of the blood or to determine a level of hemoglobin, for example. In some instances, a dye, i.e., an intercalating dye, can be used in conjunction with the spectroscopic methods to determine the presence of free nucleic acids.

A different embodiment of the imaging/delivery/evaluation catheter 200 is shown in FIGS. 2A and 2B. FIG. 2A shows a side view of an imaging/delivery/evaluation catheter 200 that uses photoacoustic members 230 as ultrasound transducers and photoreflective members 250 as ultrasound receivers for imaging. The photoacoustic member 230 is coupled to a source optical fiber 220 with blazed Bragg grating 225 (discussed below). The photoreflective member 250 is coupled to a return optical fiber 240 with blazed Bragg grating 245. Catheter 200 includes a proximal end (not shown), a mid-body (not shown), and a distal end 110 including a distal tip 115. The distal end 110 includes drug delivery lumen 120 connected to drug delivery ports 125, and guidewire lumen 130 terminating in guidewire exit 135. The distal tip 115 comprises Doppler sensor 160. The entire distal tip 110 is coated with a lubricious coating 170. The photoacoustic members 230 and photoreflective members 250 are directly in communication with the exterior of the catheter 200.

The catheter 200 employs fiber Bragg gratings (225 and 245) to couple light into or out of source and return optical fibers 220 and 240. A fiber Bragg grating is a periodic modulation of the index of refraction in a fiber. When the periodicity, d, of the modulation satisfies the Bragg condition (d=nλ/2) for a wavelength 2, that wavelength will be reflected. That is, the fiber Bragg grating acts as a wavelength-selective mirror. The degree of index change and the length of the grating influences the ratio of light reflected to that transmitted through the grating. A review of fiber Bragg gratings, including blazed Bragg gratings can be found at A. Othonos, Rev. Sci. Inst., 68 (12), 4309 (1997), incorporated by reference herein in its entirety.

As shown in FIG. 2A, the blazed Bragg grating 225 couples light from the source optical fiber 220 out of the fiber and into the photoacoustic member 230, whereupon the photoacoustic member 230 produces acoustic energy, i.e., it acts as an ultrasound transducer. This same technique can be used to produce acoustic waves for Doppler measurements, e.g., at Doppler sensor 160.

In one embodiment, the photoacoustic member 230 has a thickness in the direction of propagation that increases the efficiency of emission of acoustic energy. In some embodiments, the thickness of the photoacoustic material is selected to be about one fourth of the acoustic wavelength of the material at the desired acoustic frequency ("quarter wave matching"). Providing photoacoustic material with quarter wave matching improves the generation of acoustic energy by the photoacoustic material, resulting in improved ultrasound images. Using the quarter wave matching and sensor shaping techniques, the productivity of the fiber blazed Bragg 225 and photoacoustic member 230 approaches the productivity of piezoelectric transducers known in the field of ultrasound imaging.

In preferred embodiments, the incident light in source optical fiber 220 is pulsed at a frequency at which the acoustic waves will be produced. Light sources that produce pulses at ultrasonic frequencies, e.g., 1 MHz and greater, are commercially-available, typically solid state lasers. Nonetheless, photoacoustic materials have natural acoustic resonances, and the photoacoustic material will naturally produce a spectrum of acoustic frequencies when the material absorbs the incident light, and the photoacoustic material relaxes by producing acoustic waves. If it is desired to rely on the natural frequencies of the photoacoustic material, the incident light in source optical fiber 220 may be continuous.

The acoustic waves generated by the photoacoustic member 230 interact with tissues vasculature) in the vicinity of the distal end 110 of the catheter 200, and are reflected back (echoes). The reflected acoustic waves are collected and analyzed to obtain information about the distance from the tissues to the catheter 200, or the type of tissue, or other information, such as blood flow or pressure. The return acoustic energy can also be monitored using light via coupled optical fibers as shown in detail in FIG. 2B, where the photoreflective material 250 is in communication with the return optical fiber 240 via blazed Bragg grating 245.

The photoreflective member 250 is flexibly resilient, and is displaced by acoustic waves reflected by the tissues. A transparent (or translucent) flexible material is disposed between the return optical fiber 240 and the photoreflective member 250, thereby allowing a deflection in the photoreflective member 250 to change the path length of the light between the return optical fiber 240 and the photoreflective member 250. In alternative embodiments, a void can be left between the return optical fiber 240 and the photoreflective member 250. The dashed curved line in the photoreflective members 250 in FIG. 2B is intended to show the extent of possible deflection of the photoreflective material, e.g., with absorption of acoustic energy.

In the absence of incident acoustic energy, the photoreflective material will be in a neutral position, providing a baseline path length between the return optical fiber 240 and the photoreflective member 250. Incident light, transmitted via the return optical fiber 240, will be reflected from the photoreflective member 250, and return to a detector at the proximal end of the catheter 200 (not shown) with a characteristic round trip time. The light transmitted via the return optical fiber 240 may be the same light as used to produce acoustic energy (discussed above) or a different light (wavelength, pulse frequency, etc.) may be used. When the photoreflective member 250 is deflected, i.e., with the absorbance of incident acoustic waves, the path length between the return optical fiber 240 and the photoreflective member 250 will change, resulting in a measurable change in the properties of the reflected light, as measured by a detector at the proximal end of catheter 200 (not shown). The change may be a shift in the time of the return trip, or the shift may be an interferometric measurement. The change in the properties of the reflected light can then be analyzed to determine properties of the tissues from which the acoustic waves were reflected.

The catheter 200 can be fabricated with various techniques. In an embodiment, the catheter 200 is assembled, such as by binding the optical fibers 220 and 240 to the device and adding coating 170. The photoacoustic member 230 is then integrated into the device 200 by etching or grinding a groove in the assembled catheter 200 above the intended location of the blazed Bragg grating 245 in the source optical fiber 220. As discussed above, the depth of the groove in the assembled catheter 200 can play a role in the efficiency of the acoustic wave production (e.g., quarter wave matching). After the photoacoustic member 230 location has been defined, the blazed Bragg grating 225 can be added to the source optical fiber 220. In one example, the grating 225 is created using an optical process in which the portion of the source optical fiber 220 is exposed to a carefully controlled pattern of UV radiation that defines the blazed Bragg grating 225. After the blazed Bragg grating 225 is complete, a photoacoustic material is deposited or otherwise added over the blazed Bragg grating 225 to complete the photoacoustic member 230. An exemplary photoacoustic material is pigmented polydimethylsiloxane (PDMS), such as a mixture of PDMS, carbon black, and toluene. The photoacoustic materials may naturally absorb the light from the source optical fiber 220, or the photoacoustic material may be supplemented with dyes, e.g., organic dyes, or nanomaterials (e.g., quantum dots) that absorb the light strongly. The photoacoustic material can also be "tuned" to selectively absorb specific wavelengths by selecting suitable components.

While not shown in the figures, the described catheters may include radiopaque markers at various locations on or within the catheter to identify structures, e.g., with fluoroscopy. The radiopaque markers will be small in most instances, having a longitudinal dimension of less than 5 mm, e.g., less than 4 mm, e.g., less than 3 mm, e.g., less than 2 mm, e.g., less than 1 mm. The radiopaque markers will be at least 0.2 mm, e.g., at least 0.3 mm, e.g., at least 0.4 mm, e.g., at least 0.5 mm. The radiopaque markers may vary in axial size or diameter, depending upon their shape; however it will necessarily be small enough to fit within a catheter, e.g., catheter 100 or 200. The radiopaque markers may be constructed from any material that does not transmit x-rays and has suitable mechanical properties, including platinum, palladium, rhenium, tungsten, and tantalum.

An alternative embodiment is an aspiration catheter 300, suitable for imaging, aspirating, and sensor measurement. The distal end 110 of the aspiration catheter 300 is shown in FIGS. 3A and 3B. FIG. 3A shows a side view of the aspiration catheter 300 that uses piezoelectric elements as ultrasound transducers 140 and ultrasound receivers 150 to produce and receive ultrasound energy for imaging. Catheter 300 includes a proximal end (not shown), a mid-body (not shown), and a distal end 110 including a distal tip 115. The distal end 110 includes an aspiration lumen 128 connected to an aspiration port 127, and guidewire lumen 130 terminating in guidewire exit 135. The aspiration lumen 128 runs to the proximal end of the catheter, and is connected to a vacuum source exterior to the catheter 300. The distal tip 115 comprises Doppler sensor 160. The entire distal end 110 is coated with a lubricious coating 170, and a suitable ultrasound transparent material is used to cover the ultrasound transducers 140 and ultrasound receivers 150.

As can be seen more clearly in FIG. 3B, the transducers 140 and receivers 150 are coaxially located with the aspiration lumen 128 to maximize the inside diameter of the aspiration lumen 128 with respect to the diameter of the distal end 110 of the device. This detail can also be seen in FIG. 4B, which depicts a cross section from A to A in FIG. 1A. Other embodiments of the invention need not adopt this design. For example aspiration lumen may run to one side of the ultrasound transducers 140 and receivers 150.

The Doppler sensor 160, located in the distal tip 115 of the device allows a physician to observe blood flow in proximity to the tissues being imaged and aspirated. The Doppler sensor is electrically connected (not shown) to the proximal end of the device, which provides power for the sensor and a return path for recovering measurements. Typically, the sensor produces ultrasound in the range of 5 to 15 MHz, e.g., about 12 MHz. In other embodiments, the Doppler sensor may be replaced with an acoustic therapy transducer (not shown) to deliver acoustic waves to a tissue being treated. Acoustic therapy transducers typically operate in the range of 100 kHz and 5 MHz. Because the Doppler sensor and the acoustic therapy transducers are rather small, it is also possible for a device to include both a Doppler sensor and an acoustic therapy transducer.

A distal end view of catheter 100 and catheter 200 is identical, as shown in FIG. 4A. Regarding FIG. 4A, two drug delivery ports 125, the Doppler sensor 160, and the guidewire exit 135 are visible at the distal tip 115. This design allows the catheter 100/200 to be guided to a tissue in need of treatment along a guidewire, a therapeutic delivered to the tissue, and the results of the therapy (e.g., flow increase) evaluated with the Doppler sensor 160. In other embodiments, the distal tip 115 may include a separate transducer to provide acoustic therapy (not shown). In other embodiments, the distal tip 115 may include a lens coupled to an optical fiber (not shown) to allow phototherapy to be delivered, or to provide photoactivation of a therapeutic agent.

Cross-sectional views of catheters 100 and 200 are shown in FIGS. 4B and 4C, respectively. FIG. 4B corresponds to the cross-section taken at line AA in FIG. 1A, and FIG. 4C corresponds to the cross-section taken at line BB in FIG. 2A. Both cross sections show drug-delivery lumen 120, used to deliver a therapeutic to tissues in need thereof. FIG. 4B also shows ultrasound transducers 140, surrounding drug-delivery lumen 120, and guidewire lumen 130.

FIG. 4C shows photoacoustic member 230, source optical fiber 220, photoreflective members 250 and return optical fibers 240, corresponding to catheter 200. As shown in FIG. 4C, the photoacoustic member 230 and the photoreflective members 250 are substantially in communication with the exterior of the catheter. The photoacoustic member 230 and the photoreflective members 250 are also coupled to the respective optical fibers, i.e., with blazed Bragg gratings, as discussed above. While not shown in FIGS. 4B and 4C, one or more power/signal wires will also pass through the cross sectional view, providing power to, and receiving signals from, Doppler sensor 160. Embodiments having an additional fiber running to the distal tip 115, for example to produce acoustic energy using an additional photoacoustic material, will also run through the cross sections shown in FIGS. 4B and 4C. While not shown herein, it is possible to stagger a plurality of photoacoustic members 230 and photoreflective members 250 longitudinally along the length of catheter 200 to provide greater radial coverage. Alternatively, the catheter 200 may be rotated during imaging to provide improved image quality or to avoid blind spots due to the configuration of the photoacoustic members 230 and photoreflective members 250.

Other embodiments may combine delivery therapies with optical coherence tomography (OCT) imaging. In OCT, light from a broad band light source or tunable laser source is split by an optical fiber splitter with one fiber directing light to the distal end of a catheter, e.g., for imaging a tissue, and the other fiber directing light to a reference mirror. The distal end of the optical fiber is interfaced with the distal end of a catheter for interrogation of tissues, etc. The light emerges from the optical fiber and is reflected from the tissue being imaged. The reflected light from the tissue is collected with the optical fiber and recombined with the signal from the reference mirror forming interference fringes (measured by a detector) allowing precise depth-resolved imaging of the tissue on a micron scale.

An alternative embodiment, configured to image the tissues with OCT is shown in FIGS. 5A and 5B. FIG. 5A shows a side view of an imaging/delivery/evaluation catheter 500 that rotational OCT imaging to evaluate tissues before and after treatment. Catheter 500 includes a proximal end (not shown), a mid-body (not shown), and a distal end 110 including a distal tip 115. The distal end 110 includes drug delivery lumen 120 connected to drug delivery ports 125, and guidewire lumen 130 terminating in guidewire exit 135. The distal tip 115 comprises Doppler sensor 160. The entire distal end 110 is coated with a lubricious coating 170, and a suitable ultrasound transparent material is used to cover the ultrasound transducers 140 and ultrasound receivers 150.

Catheter 500 includes rotational element 320 and mirror 330 which direct light out of an optical fiber (not shown) and collect light that scatters off of the imaged tissue for the purpose of creating tissue measurements using the technique of optical coherence tomography (OCT), OCT typically uses a superluminescent diode source or tunable laser source emitting a 400-2000 nm wavelength, with a 50-250 nm band width (distribution of wave length) to make in-situ tomographic images with axial resolution of 2-20 µm and tissue penetration of 2-3 mm. The near infrared light sources used in OCT instrumentation can penetrate into heavily calcified tissue regions characteristic of advanced coronary artery disease. With cellular resolution, application of OCT may be used to identify other details of the vulnerable plaque such as infiltration of monocytes and macrophages. In short, application of OCT can provide detailed images of a pathologic specimen without cutting or disturbing the tissue.

The rotational element 320 may only rotate, or the rotational element 320 may translate and rotate, i.e., pull-back imaging. The principles of pull-back OCT devices are described in detail in U.S. Pat. No. 7,813,609 and US Patent Publication No. 200900431911 both of which are incorporated herein by reference in their entireties.

Because of the presence of the rotational element 320, the drug delivery lumen 120 is axially displaced. Other embodiments of the invention need not adopt this design. For example, drug delivery lumen 120 may comprise multiple lumens that are arranged about rotational element 320 to provide adequate throughput for the delivery of therapeutic agents, typically formulated as a liquid. Additionally, while the views of FIGS. 5A and 5B depict six drug delivery ports 125, this number is arbitrary. The drug delivery lumen 120 merely needs one or more exit ports to allow the therapeutic to be delivered external to the distal end 110.

The Doppler sensor 160, located in the distal tip 115 of the device allows a physician to observe blood flow in proximity to the tissues being imaged and treated. The Doppler sensor is electrically connected (not shown) to the proximal end of the device, which provides power for the sensor and a return path for recovering measurements. Typically, the sensor produces ultrasound in the range of 5 to 15 MHz, e.g., about 12 MHz. In other embodiments, the Doppler sensor may be replaced with an acoustic therapy transducer (not shown) to deliver acoustic waves to a tissue being treated. Acoustic therapy transducers typically operate in the range of 100 kHz and 5 MHz. Because the Doppler sensor and the acoustic therapy transducers are rather small, it is also possible for a device to include both a Doppler sensor and an acoustic therapy transducer.

The corresponding proximal end 610 of a catheter 600 is shown in FIG. 6. The proximal end 610 is not inserted into the body, and includes a drug delivery branch 620, essentially a tube, and a port 630, which may comprise a Luer lock or other compatible interface for attaching to a container, e.g., a syringe, containing the therapeutic to be delivered. The drug delivery branch 620 connects to drug delivery lumen 120, which runs the length of the catheter 600 to a distal end, which may correspond to FIGS. 1-5. The embodiment depicted in FIG. 6 is also suitable for use with other embodiments requiring different or additional fluidic communication, such as an aspiration catheter or a balloon catheter needing an inflation fluid. In some instances, the proximal end may comprise the drug delivery branch 620 and in addition to a similar fabricated aspiration branch (not shown).

The proximal end 610 will also include one or more electrical connections 145 in communication with electrical components at the distal end, e.g., ultrasound transducer 140, ultrasound receiver 150, or Doppler sensor 160. The proximal end 610 may further comprise one or more optical fibers 165 in optical communication with optical components at the distal end, e.g., photoacoustic member 230, photoreflective member 250 or an embodiment of the Doppler sensor 160 including a photoacoustic material. The electrical connections 145 and/or the optical fibers 165 exit the proximal end 610 of the catheter 600 at or near the proximal tip, where they are coupled to electro-optical components for imaging and evaluation. In some embodiments, the electrical connections 145 and/or the optical fibers 165 are bundled into a pigtail 723 having a connector designed to interconnect with a Patient Interface Module (PIM), discussed below.

Figure 7:
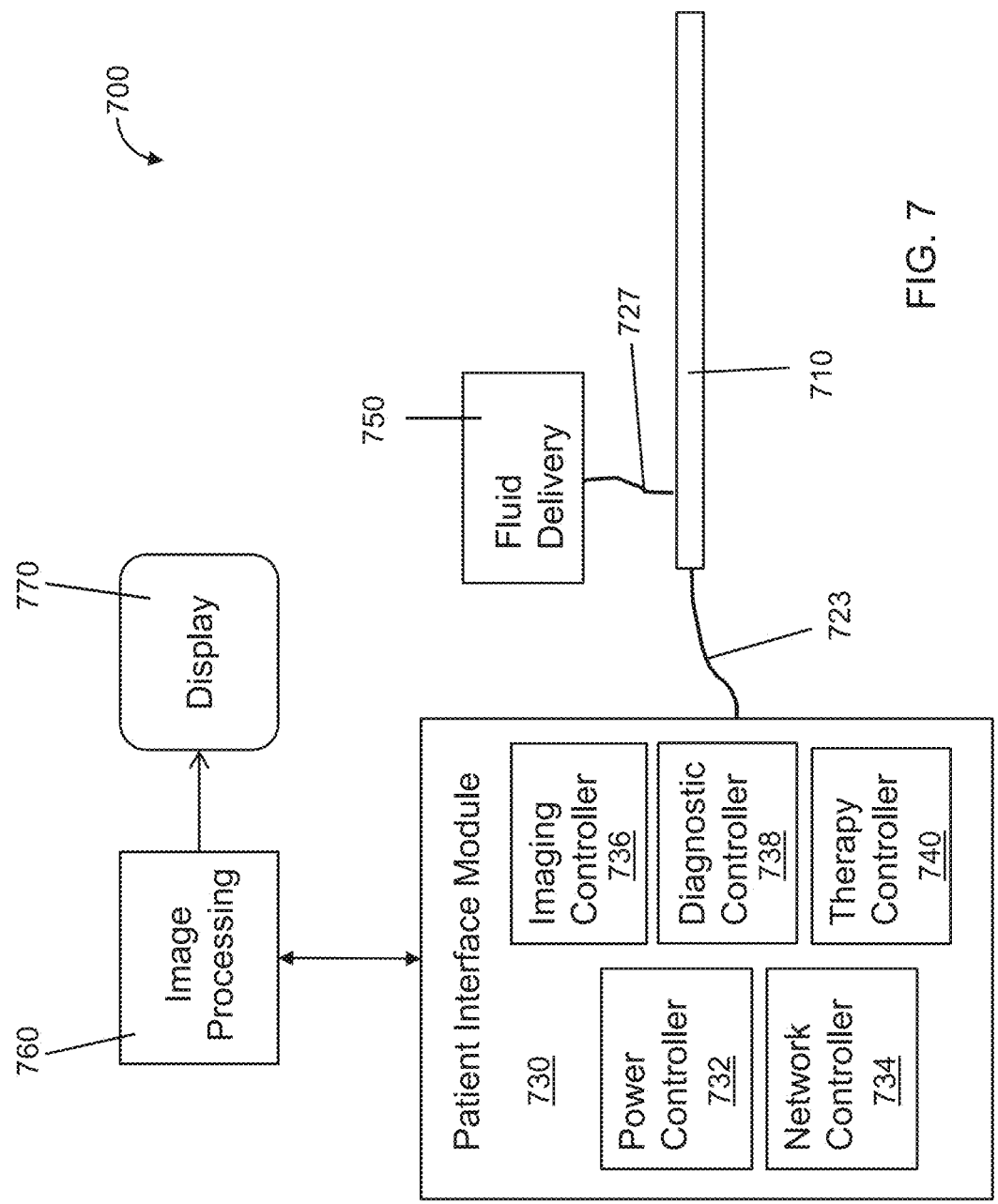
FIG. 7 depicts a system including a catheter of the invention.

A system 700, including a multifunction catheter 710, is shown in FIG. 7. As discussed above, the catheter 710 may include a pigtail 723, including the needed electrical/optical connections, and a fluid delivery branch 727. The pigtail 723 is connected to a Patient Interface Module (PIM) 730 that provides the needed signals to produce acoustic energy for imaging and therapy, and receives the return signals to produce images of the tissues or to diagnose the environment in proximity to the tissues.

As shown in FIG. 7, the PIM 730 comprises multiple components, each controlling an aspect of the task. The power controller 732 receives power from an external source and conditions or modifies the power, as needed, to drive a transducer or to power a light source. The network controller 734 allows the PIM 730 to communicate with outside components, such as image processing 730 (discussed below). The network controller 734 may be configured to operate wirelessly (e.g., WIFI or 4G), with a wired connection, or through an optical connection, which will allow MHz signals to be processed easier away from the PIM 730. The imaging controller 736 will coordinate production of acoustic energy and reception of the reflected energy, as needed to image the tissues. The imaging controller may control one or more light sources as needed for photoacoustic generation and photoreflective reception. The diagnostic controller 738 will coordinate measurement of diagnostic values, such as blood flow, blood pressure, temperature, or blood oxygenation, for example by interacting with Doppler sensor 160. The therapy controller 740 will control therapy delivery, for example acoustic or photo therapy, delivered with the distal end of the catheter 710.

In embodiments using optical fibers, such as catheter 200, the source light and the return light may be coupled or split with fiber couplers, dichroics, and filters as necessary to achieve the desired performance. Additionally, multiple light sources may be used or only a single light source. Furthermore, a particular fiber need not be limited to a single light source, as some fibers can support multiple wavelengths simultaneously and the wavelengths can be separated for analysis using known multiplexing techniques. These functions will be controlled by the imaging controller 736.

The sources of light may be any known light source configured to produce light with the desired temporal and frequency characteristics, for example, solid-state lasers, gas lasers, dye lasers, or semiconductor lasers. The sources may also be LED or other broadband sources, provided that the sources are sufficiently powerful to drive the photoacoustic transducers. In some instances the imaging controller 736 will gate the sources to provide the needed temporal resolution. In other instances, the sources will inherently provide short pulses of light at the desired frequency, e.g., 20 MHz, and the imaging controller will synchronize other imaging tasks to this natural frequency. Embodiments using optical fibers for acoustic signal collection will additionally include a detector (not shown) coupled to return fiber 240. The detector will be used to monitor changes to the coupled light to determine how the acoustic environment of the catheter 200 is changing. The detector may be a photodiode, photomultiplier tube, charge coupled array, microchannel detector, or other suitable detector. The detector may directly observe shifts in return light pulses, e.g., due to deflection of the photoreflective material, or the detector may observe interferometric changes in the returned light due to changes in path length or shape. Fourier transformation from time to frequency can also be used to improve the resolution of the detection.

At least a portion of the output from the PIM 730 will be directed to image processing 760 prior to being output to a display 770 for viewing. The image processing will deconvolve received signals to produce distance and/or tissue measurements, and those distance and tissue measurements will be used to produce an image, for example an intravascular ultrasound (IVUS) image. The image processing may additionally include spectral analysis, i.e., examining the energy of the returned acoustic signal at various frequencies. Spectral analysis is useful for determining the nature of the tissue and the presence of foreign objects. A plaque deposit, for example, will typically have a different spectral signature than nearby vascular tissue without such plaque, allowing discrimination between healthy and diseased tissue. Also a metal surface, such as a stent, will have a different spectral signal. Such signal processing may additionally include statistical processing (e.g., averaging, filtering, or the like) of the returned ultrasound signal in the time domain. Other signal processing techniques known in the art of tissue characterization may also be applied.

Other image processing may facilitate use of the images or identification of features of interest. For example, the border of a lumen may be highlighted or plaque deposits may be displayed in a visually different manner (e.g., by assigning plaque deposits a discernible color) than other portions of the image. Other image enhancement techniques known in the art of imaging may also be applied. In a further example, similar techniques can be used to discriminate between vulnerable plaque and other plaque, or to enhance the displayed image by providing visual indicators to assist the user in discriminating between vulnerable and other plaque. Other measurements, such as flow rates or pressure may be displayed using color mapping or by displaying numerical values.

As shown in FIG. 7, a fluid delivery device 750 will be coupled to the fluid delivery branch 727 to allow a physician to deliver one or more therapeutics to tissues needing treatment. Alternatively, the fluid delivery device 750 can be used to deliver an inflation fluid (e.g., saline) to an angioplasty balloon or an ablation balloon. The fluid delivery device 750 can be any suitable container for delivering a fluid, e.g., a therapeutic agent, typically in a liquid form. The fluid delivery device 750 may be a syringe, a pump, an IV bag, and ampule, or a vial. In some embodiments, the fluid delivery device 750 is a syringe pump that is interfaced to the PIM, allowing the flow of therapeutics to be coordinated with other activities, e.g., acoustic therapy or photoactivation.

In other embodiments, a system may comprise a vacuum aspiration pump or additional mechanical components, e.g., rotary power, as needed to achieve the desired procedures.

Figure 8A:
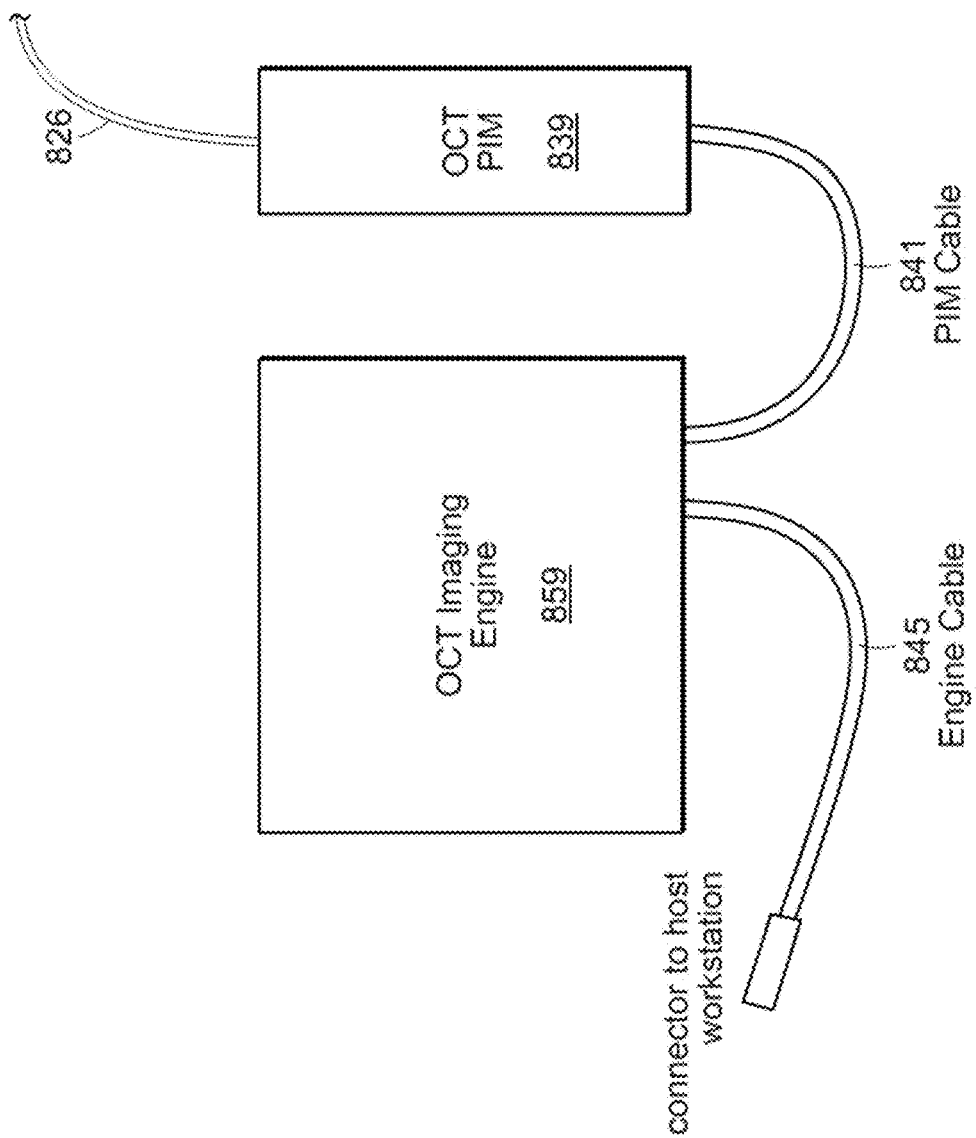
FIG. 8A is a diagram of components of an optical coherence tomography (OCT) subsystem.
Figure 8B:
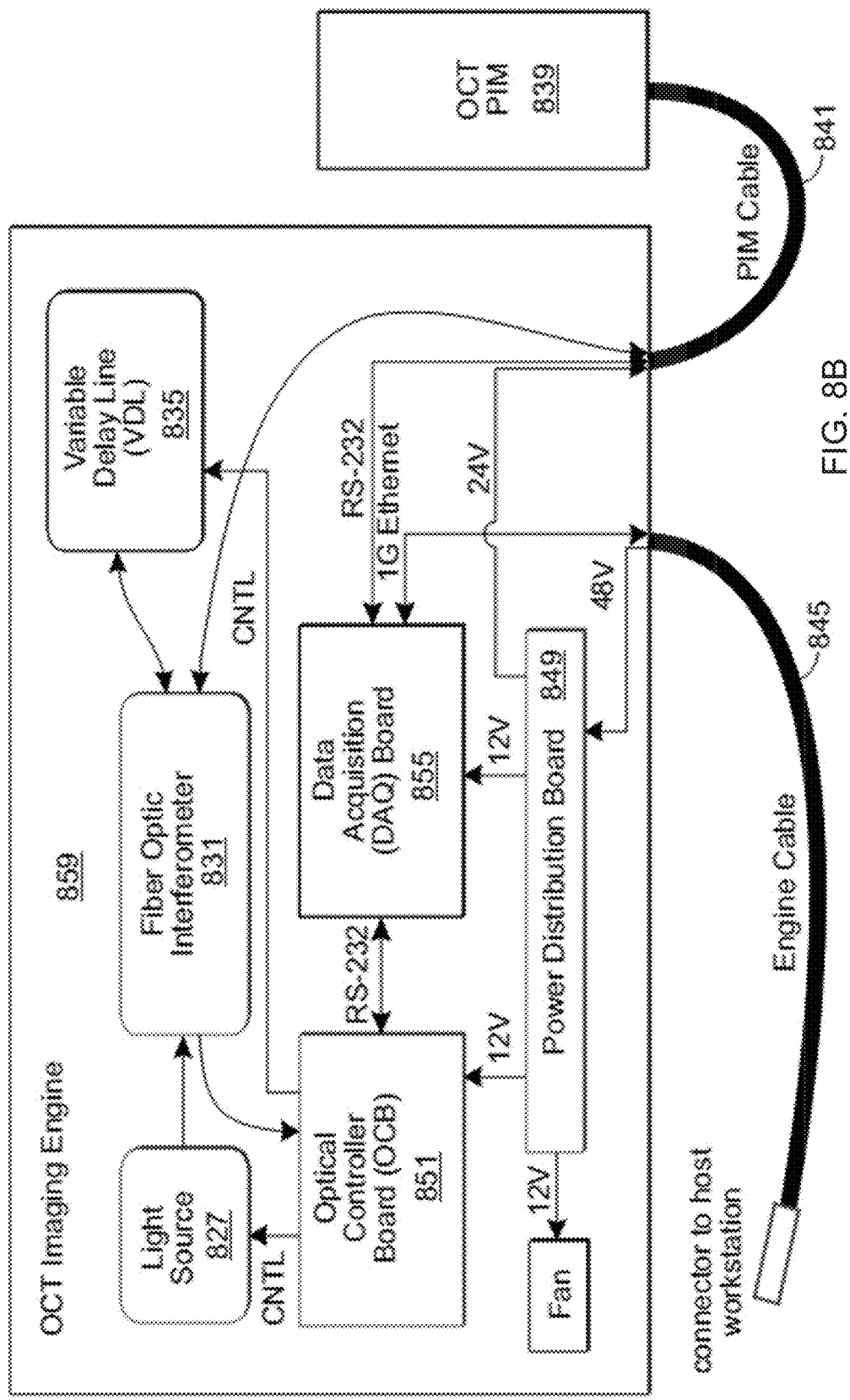
FIG. 8B is a diagram of the imaging engine shown in FIG. 8B.

In embodiments using OCT, the system 700 will additionally comprise an OCT subsystem, depicted in FIGS. 8A and 8B. Generally, an OCT system comprises three components which are 1) an imaging catheter 2) OCT imaging hardware, 3) host application software. When utilized, the components are configured to obtain OCT data, process OCT data, and transmit captured data to a host system. OCT systems and methods are generally described in Milner et al., U.S. Patent Application Publication No. 2011/0152771, Condit et al., U.S. Patent Application Publication No. 2010/0220334, Castella et al., U.S. Patent Application Publication No. 2009/0043191, Milner et al., U.S. Patent Application Publication No. 2008/0291463, and Kemp, N., U.S. Patent Application Publication No. 2008/0180683, the content of each of which is incorporated by reference in its entirety. In certain embodiments, systems and methods of the invention include processing hardware configured to interact with more than one different three dimensional imaging system so that the tissue imaging devices and methods described here in can be alternatively used with OCT, IVUS, or other hardware.

In OCT, a light source delivers a beam of light to an imaging device to image target tissue. Light sources can be broad spectrum light sources, or provide a more limited spectrum of wavelengths, e.g., near infra-red. The light sources may be pulsed or continuous wave. For example the light source may be a diode (e.g., superluminescent diode), or a diode array, a semiconductor laser, an ultrashort pulsed laser, or supercontinuum light source. Typically the light source is filtered and allows a user to select a wavelength of light to be amplified. Wavelengths commonly used in medical applications include near-infrared light, for example between about 800 nm and about 1700 nm. Methods of the invention apply to image data obtained from obtained from any OCT system, including OCT systems that operate in either the time domain or frequency (high definition) domain.

In time-domain OCT, an interference spectrum is obtained by moving a scanning optic, such as a reference mirror, longitudinally to change the reference path and match multiple optical paths due to reflections of the light within the sample. The signal giving the reflectivity is sampled over time, and light traveling at a specific distance creates interference in the detector. Moving the scanning mechanism laterally (or rotationally) across the sample produces reflectance distributions of the sample (i.e., an imaging data set) from which two-dimensional and three-dimensional images can be produced.

In frequency domain OCT, a light source configured to emit a range of optical frequencies passes through an interferometer, where the interferometer combines the light returned from a sample with a reference beam of light from the same source, and the intensity of the combined light is recorded as a function of optical frequency to form an interference spectrum. A Fourier transform of the interference spectrum provides the reflectance distribution along the depth within the sample.

Several methods of frequency domain OCT are described in the literature. In spectral-domain OCT (SD-OCT), also sometimes called "Spectral Radar" (Optics Letters, vol. 21, No. 14 (1996) 1087-1089), a grating or prism or other means is used to disperse the output of the interferometer into its optical frequency components. The intensities of these separated components are measured using an array of optical detectors, each detector receiving an optical frequency or a fractional range of optical frequencies. The set of measurements from these optical detectors forms an interference spectrum (Smith, L. M. and C. C. Dobson, Applied Optics vol. 28: (1989) 3339-3342), wherein the distance to a scatterer is determined by the wavelength dependent fringe spacing within the power spectrum. SD-OCT has enabled the determination of distance and scattering intensity of multiple scatters lying along the illumination axis by analyzing the exposure of an array of optical detectors so that no scanning in depth is necessary.

Alternatively, in swept-source OCT, the interference spectrum is recorded by using a source with adjustable optical frequency, with the optical frequency of the source swept through a range of optical frequencies, and recording the interfered light intensity as a function of time during the sweep. An example of swept-source OCT is described in U.S. Pat. No. 5,321,501.

Time- and frequency-domain systems can further vary based upon the optical layout of the systems: common beam path systems and differential beam path systems. A common beam path system sends all produced light through a single optical fiber to generate a reference signal and a sample signal whereas a differential beam path system splits the produced light such that a portion of the light is directed to the sample and the other portion is directed to a reference surface. Common beam path systems are described in U.S. Pat. No. 7,999,938; U.S. Pat. No. 7,995,210; and U.S. Pat. No. 7,787,127 and differential beam path systems are described in U.S. Pat. No. 7,783,337; U.S. Pat. No. 6,134,003; and U.S. Pat. No. 6,421,164, the contents of each of which are incorporated by reference herein in their entireties.

In certain embodiments, the invention provides a differential beam path OCT system with intravascular imaging capability as illustrated in FIG. 8A. For intravascular imaging, a light beam is delivered to the vessel lumen via a fiber-optic based imaging catheter 826, which is a multi-function catheter of the invention. The imaging catheter is connected through hardware to software on a host workstation. The hardware includes imagining engine 859 and a handheld patient interface module (PIM) 839 that includes user controls. The proximal end of imaging catheter 826 is connected to PIM 839, which is connected to imaging engine 859 as shown in FIG. 8A.

An embodiment of imaging engine 859 is shown in FIG. 8B. Imaging engine 859 (i.e., the bedside unit) houses power distribution board 849, light source 827, interferometer 831, and variable delay line 835 as well as a data acquisition (DAQ) board 855 and optical controller board (OCB) 851. PIM cable 841 connects imagining engine 859 to PIM 839 and engine cable 845 connects imaging engine 859 to the host workstation (not shown).

Figure 9:
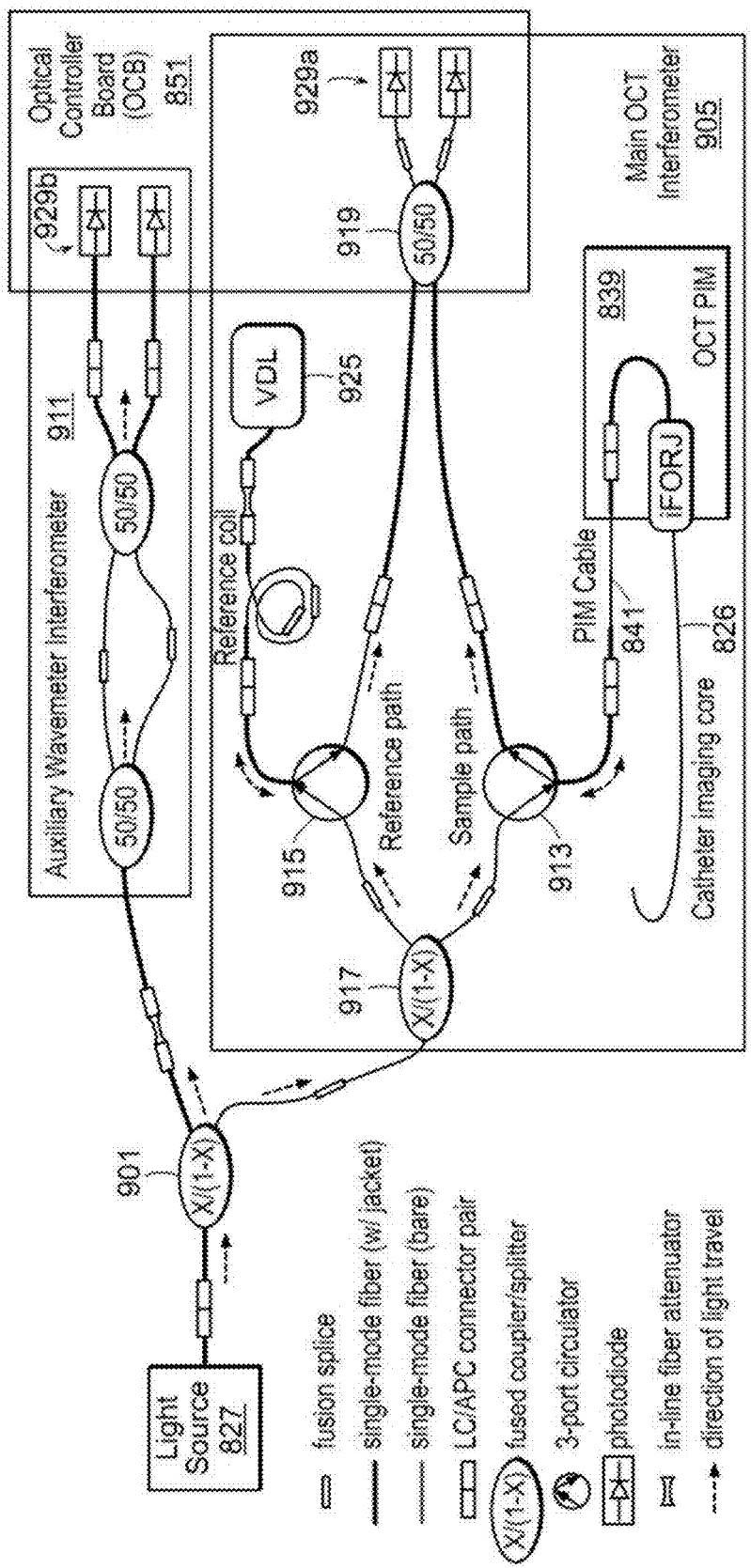
FIG. 9 is a diagram of a light path in an OCT system of certain embodiments of the invention.

FIG. 9 shows an exemplary light path in a differential beam path system which may be used in an OCT system suitable for use with the invention. Light for producing the measurements originates within light source 827. This light is split between main OCT interferometer 905 and auxiliary interferometer 911. In some embodiments, the auxiliary interferometer is referred to as a "clock" interferometer. Light directed to main OCT interferometer 905 is further split by splitter 917 and recombined by splitter 919 with an asymmetric split ratio. The majority of the light from splitter 917 is guided into sample path 913 while the remainder goes into reference path 915. Sample path 917 includes optical fibers running through PIM 839 and imaging catheter core 826 and terminating at the distal end of the imaging catheter, where the sample is measured.

The reflected light is transmitted along sample path 913 to be recombined with the light from reference path 915 at splitter 919. A variable delay line (VDL) 925 on the reference path uses an adjustable fiber coil to match the length of reference path 915 to the length of sample path 913. The reference path length is adjusted by a stepper motor translating a mirror on a translation stage under the control of firmware or software.

The combined light from splitter 919 is split into orthogonal polarization states, resulting in RF-band polarization-diverse temporal interference fringe signals. The interference fringe signals are converted to photocurrents using PIN photodiodes 929a, and 929b, on optical controller board (OCB) 851. The interfering, polarization splitting, and detection steps are done by a polarization diversity module (PDM) (not shown) on OCB 851. Signal from OCB 851 is sent to DAQ 855, shown in FIG. 9. DAQ 855 includes a digital signal processing (DSP) microprocessor and a field programmable gate array (FPGA) to digitize signals and communicate with the host workstation and PIM 839. The FPGA converts raw optical interference signals into meaningful reflectivity measurements. DAQ 855 also compresses data as necessary to reduce image transfer bandwidth, e.g., to 1 Gbps, e.g., by compressing frames with a glossy compression JPEG encoder.

Additional embodiments of the invention including other combinations of imaging, treatment and assessment will be evident to those of skill in the art in view of this disclosure and the claims below.

INCORPORATION BY REFERENCE

References and citations to other documents, such as patents, patent applications, patent publications, journals, books, papers, and web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. An intravascular device comprising:
a ring-shaped transducer array located at a distal end of the intravascular device, wherein the ring-shaped transducer array is configured to image a tissue;
a therapy lumen located at the distal end of the intravascular device, wherein the therapy lumen passes through the ring-shaped transducer array and terminates in a therapy port that is configured to deliver a therapy to a tissue; and
a sensor located distal to the therapy port at a distal-most tip of the distal end of the intravascular device, wherein the sensor is separate from the ring-shaped transducer array and is configured to measure blood flow in an environment associated with the tissue.

2. The device of claim 1, wherein the therapy lumen passing through the ring-shaped transducer array is a drug delivery lumen configured to deliver a drug through the therapy lumen.

3. The device of claim 1, wherein the therapy lumen passing through the ring-shaped transducer array is an aspiration lumen configured to aspirate tissue through the therapy lumen.

4. The device of claim 1, wherein the device is additionally configured to make at least one spectroscopic measurement selected from the group consisting of infrared absorption, visible absorption, Raman, and fluorescence.

5. The device of claim 1, wherein the device is a catheter.

6. The device of claim 1 wherein the ring-shaped transducer array is located proximal to the therapy port and is aligned coaxially with a central axis of the therapy lumen within the distal end of the intravascular device.

7. The device of claim 1 wherein the ring-shaped transducer array surrounds a long axis of the therapy lumen within the distal end of the intravascular device to thereby maximize an inside diameter of the therapy lumen with respect to a diameter of the distal end of the device.

8. The device of claim 1 wherein the ring-shaped transducer array comprises a plurality of ultrasonic transmitters and a plurality of ultrasonic receivers that cooperate to image the tissue.

9. The device of claim 8 wherein the ring-shaped transducer array surrounds a long axis of the therapy lumen to thereby maximize an inside diameter of the therapy lumen.

10. The device of claim 8 wherein the ring-shaped transducer array is coaxially aligned with a long axis of the therapy lumen within the distal end of the intravascular device to thereby maximize an inside diameter of the therapy lumen with respect to a diameter of the distal end of the device.

11. The device of claim 1 wherein the sensor located distal to the therapy port comprises a Doppler sensor.

12. The device of claim 1 further comprising an acoustic therapy transducer at the distal end of the device, wherein the acoustic therapy transducer is configured to deliver acoustic waves to the tissue.

13. The device of claim 1, further comprising a distal tip portion distal to the distal end, wherein the distal tip portion comprises the distal-most tip and a side surface, wherein the side surface comprises the therapy port.

14. An intravascular device for simultaneous imaging, monitoring and therapy of tissue located within a patient, the intravascular device comprising:
a ring-shaped ultrasonic transducer array located at a distal end of the intravascular device, wherein the ring-shaped ultrasonic transducer array is configured to image the tissue;
a therapy lumen in fluid communication with a proximal end and the distal end of the intravascular device, wherein the therapy lumen passes through the ring-shaped ultrasonic transducer array and terminates in a therapy port at the distal end of the intravascular device to apply a therapy to the tissue; and
a blood flow sensor located distal to the therapy port at a distal-most tip of the distal end of the intravascular device, wherein the sensor is separate from the ring-shaped ultrasonic transducer array and is configured to measure blood flow in an environment associated with the tissue.

15. The intravascular device of claim 14 wherein the blood flow sensor is a Doppler sensor.

16. The intravascular device of claim 14 further comprising an acoustic therapy transducer at the distal end of the device, wherein the acoustic therapy transducer is configured to deliver acoustic waves to the tissue, and wherein the acoustic therapy transducer is separate from the ring-shaped ultrasonic transducer array and from the blood flow sensor.

17. The intravascular device of claim 14 wherein the ring-shaped ultrasonic transducer array is located proximal to the therapy port and coaxially with a long axis of the therapy lumen within the distal end of the intravascular device.

18. The intravascular device of claim 14 wherein the ring-shaped transducer array is located proximal to the therapy port and coaxially with a long axis of the therapy lumen within the distal end of the intravascular device to thereby maximize an inside diameter of the therapy lumen with respect to a diameter of the distal end of the intravascular device.

19. The intravascular device of claim 14 wherein the ring-shaped ultrasonic transducer array comprises a plurality of ultrasonic receivers that cooperate with a plurality of ultrasonic transmitters in the ring-shaped ultrasonic transducer array to image the tissue, wherein the ring-shaped ultrasonic transducer array is located proximal to the therapy port and coaxially with a long axis of the therapy lumen within the distal end of the intravascular device to thereby maximize an inside diameter of the therapy lumen with respect to a diameter of the distal end of the device.

20. The intravascular device of claim 14 wherein the therapy lumen passing through the ring-shaped transducer array is a drug delivery lumen configured to deliver a drug to the tissue through the therapy lumen.

21. The intravascular device of claim 14 wherein the therapy lumen passing through the ring-shaped transducer array is an aspiration lumen configured to aspirate the tissue through the therapy lumen.

* * * * *